US006958814B2

(12) United States Patent
Borden et al.

(10) Patent No.: US 6,958,814 B2
(45) Date of Patent: Oct. 25, 2005

(54) APPARATUS AND METHOD FOR MEASURING A PROPERTY OF A LAYER IN A MULTILAYERED STRUCTURE

(75) Inventors: Peter G. Borden, San Mateo, CA (US); Ji Ping Li, Fremont, CA (US)

(73) Assignee: Applied Materials, Inc., Santa Clara, CA (US)

( * ) Notice: Subject to any disclaimer, the term of this patent is extended or adjusted under 35 U.S.C. 154(b) by 27 days.

(21) Appl. No.: 10/090,316

(22) Filed: Mar. 1, 2002

(65) Prior Publication Data

US 2003/0164946 A1 Sep. 4, 2003

(51) Int. Cl.$^7$ .......................... G01N 21/55; G01N 21/88
(52) U.S. Cl. ..................... 356/432; 356/445; 356/237.2
(58) Field of Search ................. 356/432, 445, 356/237.2, 237.3, 237.4, 237.5

(56) References Cited

U.S. PATENT DOCUMENTS

| | | | |
|---|---|---|---|
| 3,462,602 A | 8/1969 | Apple | 250/83.3 |
| 3,803,413 A | 4/1974 | Vanzetti et al. | 250/338 |
| 3,909,602 A | 9/1975 | Micka | 235/151.3 |
| 3,930,730 A | 1/1976 | Laurens et al. | 356/106 |
| 4,201,087 A | 5/1980 | Akita et al. | 73/339 |
| 4,243,327 A | 1/1981 | Frosch et al. | 356/432 |
| 4,255,971 A | 3/1981 | Rosencwaig | 73/606 |
| 4,455,741 A | 6/1984 | Kolodner | 29/574 |
| 4,466,748 A | 8/1984 | Needham | 374/129 |
| 4,468,136 A | 8/1984 | Murphy et al. | 374/45 |
| 4,513,384 A * | 4/1985 | Rosencwaig | 702/170 |
| 4,521,118 A | 6/1985 | Rosencwaig | 374/5 |
| 4,522,510 A | 6/1985 | Rosencwaig | 374/7 |
| 4,579,463 A | 4/1986 | Rosencwaig et al. | 374/57 |
| 4,632,561 A | 12/1986 | Rosencwaig et al. | 356/432 |

(Continued)

FOREIGN PATENT DOCUMENTS

| | | | |
|---|---|---|---|
| EP | 0 718 595 | 12/1995 | |
| JP | 05006929 A | 1/1993 | ........... H01L/21/66 |
| JP | 2000009443 A | 1/2000 | |
| WO | 97/08536 | 6/1997 | .......... G01N/21/00 |
| WO | 99/64880 | 12/1999 | .......... G01R/31/26 |
| WO | 00/07357 | 3/2000 | .......... G01R/21/17 |

OTHER PUBLICATIONS

J. Opsal, "High Resolution Thermal Wave Measurements and Imaging of Defects and Damage in Electronic Materials" Photoacoustic and Photothermal Phenomena II, Springer Series in Optical Sciences, vol. 62, Springer Verlag Berlin, Heidelberg, 1990.

(Continued)

Primary Examiner—Richard A. Rosenberger
(74) Attorney, Agent, or Firm—Silicon Valley Patent Group LLP

(57) ABSTRACT

An apparatus measures a property of a layer (such as the sheet resistance of a conductive layer) by performing the following method: (1) focusing the heating beam on the heated a region (also called "heated region") of the conductive layer (2) modulating the power of the heating beam at a predetermined frequency that is selected to be sufficiently low to ensure that at any time the temperature of the optically absorbing layer is approximately equal to (e.g., within 90% of) a temperature of the optically absorbing layer when heated by an unmodulated beam, and (3) measuring the power of another beam that is (a) reflected by the heated region, and (b) modulated in phase with modulation of the heating beam. The measurement in act (3) can be used directly as a measure of the resistance (per unit area) of a conductive pad formed by patterning the conductive layer. Acts (1)–(3) can be repeated during fabrication of a semiconductor wafer, at each of a number of regions on a conductive layer, and any change in measurement indicates a corresponding change in resistance of the layer. When the measurement changes by more than a predetermined amount (e.g., by 10%), a process parameter that controls the fabrication process is changed to return the measurement to normal in the next wafer.

34 Claims, 7 Drawing Sheets

U.S. PATENT DOCUMENTS

| | | | |
|---|---|---|---|
| 4,634,290 A | | 1/1987 | Rosencwaig .................... 374/5 |
| 4,636,088 A | * | 1/1987 | Rosencwaig et al. .......... 374/5 |
| 4,679,946 A | | 7/1987 | Rosencwaig et al. .......... 374/5 |
| 4,710,030 A | | 12/1987 | Tauc et al. ................... 356/445 |
| 4,750,822 A | * | 6/1988 | Rosencwaig et al. ....... 356/445 |
| 4,795,260 A | | 1/1989 | Schuur et al. ............... 356/400 |
| 4,950,990 A | | 8/1990 | Moulder ...................... 324/224 |
| 4,975,141 A | | 12/1990 | Greco et al. ................. 156/626 |
| 4,996,659 A | | 2/1991 | Yamaguchi et al. ......... 714/736 |
| 5,042,951 A | | 8/1991 | Gold et al. ................... 356/369 |
| 5,074,669 A | | 12/1991 | Opsal .......................... 356/447 |
| 5,128,864 A | | 7/1992 | Waggener et al. ....... 364/413.2 |
| 5,149,978 A | | 9/1992 | Opsal et al. ................. 250/234 |
| 5,159,412 A | | 10/1992 | Willenborg et al. ........ 356/445 |
| 5,181,080 A | | 1/1993 | Fanton et al. ............... 356/381 |
| 5,228,776 A | | 7/1993 | Smith et al. .................... 374/5 |
| 5,304,931 A | | 4/1994 | Flamig et al. ............... 324/309 |
| 5,377,006 A | | 12/1994 | Nakata ........................ 356/349 |
| 5,408,327 A | | 4/1995 | Geiler et al. ................ 356/432 |
| 5,430,548 A | | 7/1995 | Hirio et al. .................. 356/394 |
| 5,454,004 A | | 9/1995 | Leger ........................... 372/99 |
| 5,574,562 A | | 11/1996 | Fishman et al. ............. 356/432 |
| 5,652,716 A | | 7/1997 | Battersby ...................... 703/13 |
| 5,657,754 A | | 8/1997 | Rosencwaig ................ 128/633 |
| 5,667,300 A | | 9/1997 | Mandelis et al. ............. 374/43 |
| 5,706,094 A | * | 1/1998 | Maris .......................... 356/432 |
| 5,741,614 A | | 4/1998 | McCoy et al. ................ 430/30 |
| 5,761,082 A | | 6/1998 | Miura-Mattausch ......... 703/14 |
| 5,764,363 A | | 6/1998 | Ooki et al. ................... 356/364 |
| 5,790,251 A | | 8/1998 | Hagiwara .................... 356/351 |
| 5,877,860 A | | 3/1999 | Borden ........................ 356/376 |
| 5,883,518 A | | 3/1999 | Borden ........................ 324/752 |
| 5,966,019 A | | 10/1999 | Borden ........................ 324/752 |
| 5,978,074 A | | 11/1999 | Opsal et al. ................... 356/72 |
| 6,049,220 A | | 4/2000 | Borden et al. ............... 324/765 |
| 6,054,868 A | | 4/2000 | Borden et al. ............... 324/752 |
| 6,081,334 A | | 6/2000 | Grimbergen et al. ....... 356/357 |
| 6,154,280 A | | 11/2000 | Borden ........................ 356/376 |
| 6,169,601 B1 | | 1/2001 | Eremin et al. ........... 356/239.8 |
| 6,178,020 B1 | | 1/2001 | Schultz et al. .............. 359/107 |
| 6,281,027 B1 | | 8/2001 | Wei et al. ...................... 438/14 |
| 6,323,951 B1 | | 11/2001 | Borden et al. ............... 356/502 |
| 6,327,035 B1 | | 12/2001 | Li et al. ....................... 356/432 |
| 6,330,361 B1 | | 12/2001 | Mitchell et al. ............. 382/211 |
| 6,336,969 B1 | | 1/2002 | Yamaguchi et al. ............ 117/7 |
| 6,395,563 B1 | | 5/2002 | Eriguchi ......................... 438/7 |
| 6,400,454 B1 | | 6/2002 | Noguchi et al. ............. 356/237 |
| 6,426,644 B1 | | 7/2002 | Borden et al. ............... 324/765 |
| 6,483,594 B2 | | 11/2002 | Borden et al. ............... 356/502 |
| 6,486,965 B1 | | 11/2002 | Kim ............................. 356/626 |
| 6,489,624 B1 | | 12/2002 | Ushio et al. ............... 250/559.3 |
| 6,489,801 B1 | | 12/2002 | Borden et al. ............... 324/766 |
| 6,528,333 B1 | | 3/2003 | Jun et al. ....................... 438/16 |
| 6,559,942 B2 | | 5/2003 | Sui et al. ..................... 356/369 |
| 6,694,284 B1 | | 2/2004 | Nikoonahad et al. ....... 702/155 |
| 6,734,968 B1 | | 5/2004 | Wang et al. ................. 356/369 |
| 2002/0126732 A1 | | 9/2002 | Shakouri et al. ............. 374/130 |
| 2002/0186045 A1 | | 12/2002 | Cox ............................... 326/41 |
| 2003/0036231 A1 | | 2/2003 | Bhattacharva et al. ...... 438/201 |
| 2003/0096436 A1 | | 5/2003 | Satya et al. .................... 438/11 |
| 2003/0155927 A1 | | 8/2003 | Pinto et al. .................. 324/501 |

OTHER PUBLICATIONS

A. Rosencwaig, "Thermal Wave Measurement of Thin–Film Thickness"; 1986 American Chemical Society, pp. 182–191.

A. Rosencwaig et al., "Thin–Film Thickness Measurements with Thermal Waves"; Journal De Physique, Oct. 1983, pp. C6–483—C6–489.

W. L. Smith et al. "Thermal–wave Measurements and Monitoring of TaSIx Silicide Film Properties" J. Vac. Technol.B2(4), Oct.–Dec. 1984, pp. 710–713.

A. Salnick et al., "Nonlinear Fundamental Photothermal Response in 3D Geometry: Experimental Results for Tungsten", (believed to be prior to Mar. 1, 2002).

S. Ameri et al., "Photo–Displament Imaging", Mar. 30, 1981, pp. 337–338.

L. Chen et al., "Thermal Wave Studies of Thin Metal Films Using the Meta–Probe–A New Generation Photothermal System" 25th Review of Progress in QNDE, Snowbird, UT Jul. 19–24, 1998, pp 1–12.

P. Alpern and S. Wurm, "Modulated Optical Reflectance Measurements on Bulk Metals and Thin Metallic Layers", J. Appl. Phys. 66(4), Aug. 15, 1989, pp 1676–1679.

J. Opsal, "The Application of Thermal Wave Technology to Thickness and Grain Size Monitoring of Aluminum Films", SPIE vol. 1596 Metalization Performance and Reliability Issues for VLSI and ULSI (1991), pp 120–131.

A. Rosenwaig, "Process Control In IC Manufacturing With Thermal Waves", Review of Progress in Quantitative Nondestructive Evaluation, vol. 9, 1990, pp 2031–2037.

K. Farnaam, "Measurement of Aluminum Alloy Grain Size on Product Wafers and its Correlation to Device Reliability", 1990 WLR Final Report, pp 97–106.

B.C. Forget et al., "High Resolution AC Temperature Field Imaging", Electronic Letters 25th Sep. 1997, vol. 33 No. 20, pp 1688–1689.

C. Paddock et al., "Transient Thermoreflectance from Metal Films", May 1986 vol. 11, No. 5 Optical Letters, pp 273–275.

C. Paddock et al., "Transient Thermoreflectance from Metal Films", J. Appl. Phys. 60(1), Jul. 1, 1986, pp 285–290.

Per–Eric Nordail et al. "Photothermal Radiometry", Physica Scripts, vol. 20, 659–662, 1979.

A. Rosenwaig, "Thermal Wave Monitoring and Imaging of Electronic Materials and Devices", pp 73–109.

A. Rosenwaig, "Applications of Thermal–Wave Physics to Microelectronics", VLSI Electronics, Microstructure Science vol. 9, 1995, pp 227–288.

W. Lee Smith et al., "Voids, Notches and Microcracks in A1 Metallization Detected by Nondestructive Thermal Wave Imaging", Jun. 23, 1989, pp. 211–221.

W. Lee Smith et al., Imaging of Subsurface Defects in ULSI Metalization (A1 Voids SI Preciptates, Silicide Instability) and SI Substrates (D Defects), Technical Proceedings Simicon/Japan 1992, Nippon Convention Center, Japan pp 238–246.

W. Lee Smith, "Nondestructive Thermal Wave Imaging of Voids & Microcracks in Aluminum Metallization", 1989 WLR Final Report, pp 55–68.

W. Lee Smith, "Direct Measurement of Stress–Induced Void Growth by Thermal Wave Modulated Optical Reflectance Imaging", 1991 IEEE/IRPS, pp 200–208.

W. Lee Smith, "Evaluating Voids and Microcracks in A1 Metalization", Semiconductor International, Jan. 1990, pp 232–237.

C.G. Welles et al., "High–Resolution Thermal Wave Imaging of Surface and Subsurface Defects in IC Metals Lines", Materials Research Society, SF Marriott, Apr. 27–May 1, 1992, pp 1187–1191.

L. Fabbri et al., "Analysis of Local Heat Transfer Properties of Tape–cast AIN Ceramics Using Photothermal Reflectance Microscopy", 1996 Chapman & Hall, pp 5429–5436.

J. A. Batista et al., "Biased MOS–FET and Polycrystalline Silicon Tracks Investigated by Photothermal Reflectance Microscopy", pp 468–469.

L. Chen et al., "Meta–Probe: A New Generation Photothermal System For Thin Metal Films Characterization" (believed to be prior to Mar. 1, 2002).

L. Chen et al., "Thermal Wave Studies of Thin Metal Films and Structures", (believed to be prior to Mar. 1, 2002).

9th International Conference on Photoacoustic and Photothermal Phenomena Conference Digest, Jun. 27–30, 1996 Nanjing, P.R. China, pp 81.

R.S. Sharpe, Research Techniques in Nondestructive Testing vol. VII, Academic Press 1984, pp 158–365.

R. L. Thomas et al., "Thermal Wave Imaging For Nondestructive Evaluation" 1982 Ultrasonic Symposium, pp 586–590.

G. Slade Cargill III, "Electron–Acoustic Microscopy", Physics Today, Oct. 1981, pp 27–32.

A. Rosencwaig, "Thermal Wave Microscopy", Solid State Technology, Mar. 1982, pp 91–97.

Eric A. Ash, "Acoustical Imaging" vol. 12, Plenium Press, Jul. 19–22, 1982, pp 61–65.

Jackson, "Classical Electrodynamics", John Wiley & Sons, Inc., (month unavailable), 1967, pp. 222–226.

Rosencwaig et al. "Detection of Thermal Waves Through Optical Reflectance", Appl Phys. Lett. 46, Jun. 1985, pp1013–1015.

Rosencwaig, "Thermal–Wave Imaging", SCIENCE, vol. 218, No. 4569, Oct. 1982, pp. 223–228.

Opsal et al. "Thermal–Wave Detection and Thin–Film Thickness Measurements with Laser Beam Deflection"; Applied Optics, vol. 22, No. 20, Oct. 1983, pp. 3169–3176.

Rosencwaig, "Thermal Wave Characterization and Inspection of Semiconductor Materials and Devices", Chapter 5 (pp. 97–135) of Photoacoustic and Thermal Wave Phenomena in Semiconductors, North Holland (month unavailable) 1987.

"Process Monitoring System," Quantox Product Brochure, 3 pg, prior to Jun. 10, 1998.

J. Kolzer et al "Thermal Imaging and Measurement Techniques for Electronic Materials and Devices" Microlectronic Engineering, vol. 31, 1996 (month unknown) pp. 251–270.

C. Martinsons et al. "Recent progress in the measurement of thermal properties of hard coatings" Thin Solid Films, vol. 317, Apr. 1998, 455–457.

S. Wolf and R. N. Tauber, "Silicon Processing For The VLSI Era", vol. 1, 1986, pp. 388–399.

Yaozhi Hu and Sing Pin Tay, "Spectroscopic ellipsometry investigation of nickel silicide formation by rapid thermal process", J. Vac. Sci. Technology, American Vacuum Soc. May/Jun. 1998, pp. 1820–1824.

*Quality Today News*, article entitled *"In–Line Metrology SEM System with 3D Imaging"* dated Jan. 10, 2000 and published at http://www.qualitytoday.com/Jan.–00–news/011000–3.htm before Apr. 4, 2001.

Bristow, Thomas C. and Dag Lindquist, "Surface Measurements With A Non–Contact Nomarski–Profiling Instrument", Interferometric Metrology, SPIE vol. 816, Aug. 1987, pp. 106–110.

Walter G. Driscoll and William Vaughan, "Handbook of Optics", 1978, pp. 8–42, 8–43, 8–107, and 10–72 to 10–77.

Charles Kittel, "Introduction to Solid State Physics", Fourth Edition, John Wiley & Sons, published prior to Mar. 1, 2002, pp. 262–264.

Rolf E. Hummel, "Electronic Properties of Materials, An Introduction For Engineers", published prior to Mar. 1, 2002, pp. 137–145.

H.S. Carslaw and J.C. Jaeger, "Conduction of Heat In Solids", Second Edition, published prior to Mar. 1, 2002, pp. 64–66.

"Process Monitoring System", Quantox Product Brochure, 3 pages, published prior to Mar. 1, 2002.

* cited by examiner

APPARATUS AND METHOD FOR MEASURING A PROPERTY OF A LAYER IN A MULTILAYERED STRUCTURE

CROSS-REFERENCE TO RELATED APPLICATIONS

This application is related to and incorporates by reference in their entirety the following commonly owned, copending U.S. patent applications:

Ser. No. 08/638,944, entitled "SYSTEM AND METHOD FOR MEASURING THE DOPING CONCENTRATION AND DOPING PROFILE OF A REGION IN A SEMICONDUCTOR SUBSTRATE", filed Apr. 24, 1996, by Peter G. Borden;

Ser. No. 08/637,244, entitled "SYSTEM AND METHOD FOR MEASURING PROPERTIES OF A SEMICONDUCTOR SUBSTRATE IN A FABRICATION LINE,"filed Apr. 24, 1996, by Peter G. Borden;

Ser. No. 09/095,804 entitled "AN APPARATUS AND METHOD FOR EVALUATING A WAFER OF SEMICONDUCTOR MATERIAL", filed Jun. 10, 1998, by Peter G. Borden et al., now issued as U.S. Pat. No. 6,049,220;

Ser. No. 09/095,805 entitled "AN APPARATUS AND METHOD FOR MEASURING A PROPERTY OF A LAYER IN A MULTILAYERED STRUCTURE", filed Jun. 10, 1998, by Peter G. Borden et al., now issued as U.S. Pat. No. 6,054,868;

Ser. No. 09/521,232 entitled "EVALUATING A PROPERTY OF A MULTILAYERED STRUCTURE", filed on Mar. 8, 2000, by Peter G. Borden et al.; and Ser. No. 09/274,821 entitled "APPARATUS AND METHOD FOR DETERMINING THE ACTIVE DOPANT PROFILE IN A SEMICONDUCTOR WAFER", filed on Mar. 22, 1999, by Peter G. Borden and Regina G. Nijemijer.

Ser. No. 10/090,262, entitled "EVALUATING A MULTILAYERED STRUCTURE FOR VOIDS", filed concurrently herewith, by Peter G. Borden.

Ser. No. 10/090,287, entitled "IDENTIFYING DEFECTS IN A CONDUCTIVE STRUCTURE OF A WAFER, BASED ON HEAT TRANSFER THERETHROUGH", filed concurrently herewith, by Peter G. Borden et al.

BACKGROUND OF INVENTION

Silicide layers of sub-micron (i.e. less than 1 micron) dimensions are conventionally used in integrated circuits. Such layers can be formed in a two step process as follows. In a first step, a film of metal (such as titanium, cobalt or nickel) is deposited onto a silicon substrate, or a layer of polysilicon. In a second step, the film is annealed to form a metal-silicon compound (such as titanium silicide, cobalt silicide, or nickel silicide). Conventionally, the sheet resistance of such a silicide layer is measured on a test wafer, and the measured sheet resistance may be multiplied by a measurement of a silicide layer's thickness on a production wafer, to determine a property of the layer, called "resistivity."

A number of methods exist for measuring sheet resistance of the test wafer. In one method, four probes are brought into physical contact with the silicide layer, to measure the layer's sheet resistance directly. See, for example, "The Four-Point Probe", Section 1.2, pages 2–20 in the book "Semiconductor Material and Device Characterization" by Dieter K. Schroder, John Wiley & Sons, Inc., New York, 1990. The just-described method requires the silicide layer to have an area (e.g., 5 square mm) that may be several orders of magnitude larger than the area of a silicide layer after etching (e.g., <0.5 square microns). Due to such a requirement on the size of the silicide layer (to have a $10^8$ times larger area), and the need to contact the silicide layer, such measurements are performed prior to patterning (i.e. typically on a test wafer).

Many methods, such as spectroscopic ellipsometry, Rutherford backscattering (RBS), scanning electron microscopy and energy dispersive x-ray spectrometry can also be used to determine the sheet resistance, as described in, for example, an article entitled "Spectroscopic ellipsometry investigation of nickel silicide formation by rapid thermal process" by Yaozhi Hu and Sing Pin Tay, Journal of Vacuum Science Technology, volume 16, no. 3, published May/June 1998 by the American Vacuum Society.

U.S. Pat. No. 5,228,776 granted to Smith et al. (hereinafter "Smith") describes measuring changes in optical reflectivity (column 4, line 5–6) caused by thermal waves (column 3, line 42) to "monitor variations in electrical conductivity and resistance . . . " (column 4, lines 53–54). Specifically, Smith requires "periodically exciting the sample at a highly localized spot on the sample surface . . . The pump beam functions to periodically heat the sample which in turn generates thermal waves that propagate from the irradiated spot . . . Features at or beneath the sample surface can be studied by monitoring the variations they induce in these waves" (column 1, lines 25–40). Note also that Smith requires the pump and probe beams to be non-coincident and non-coplanar.

Smith also states that "when the optical reflectivity of the sample is to be monitored, it is desirable to arrange the pump and probe beams to be coincident on the sample" (column 1, lines 60–64). When using such coincident beams, Smith notes problems created by "surfaces associated with defective vias are often not optically flat . . . " (column 3, lines 6–13). Moreover, prior art also states that "[w]hen materials other than semiconductors are to be evaluated, such as metals . . . analysis of the thermal wave patterns is required" (see U.S. Pat. No. 4,854,710 at column 7, lines 41–44).

See also U.S. Pat. No. 5,978,074 granted to Opsal et al.

SUMMARY OF THE INVENTION

In accordance with the principles of this invention, an apparatus and method focus a beam of electromagnetic radiation (also called "heating beam") on a region (also called "heated region") of an optically absorbing layer (i.e., a layer that is not transparent, but may be partially transparent, e.g. 99% absorbing and 1% transmitting or vice versa) in a multilayered structure, such that at least a portion of the energy of the heating beam is transformed into heat in the optically absorbing layer. The heating beam's intensity is modulated at a frequency that is sufficiently low to ensure that at any time the temperature of the optically absorbing layer is approximately equal to (e.g., within 90% of) another temperature of the optically absorbing layer obtained by heating with by an unmodulated beam (i.e. a beam having constant power, equal to the instantaneous power of the modulated beam).

In the multilayered structure under evaluation (by the apparatus and method as described herein), a layer (also called "underlying layer" which can be, e.g. the substrate or an ion implemented region in the substrate) that is located in contact with the optically absorbing layer is thermally conductive. In one embodiment, the optically absorbing layer is less thermally conductive than the underlying layer. In one example of such an embodiment, the optically absorbing layer includes one or more silicides formed by annealing a layer of metal (such as nickel, cobalt or titanium) deposited on an underlying silicon layer. In another example of such embodiment, the optically absorbing layer includes a heavily doped layer of polycrystalline silicon.

In both examples, the amount of heat generated in the optically absorbing layer increases as an exponential function of the product of two properties $\alpha z$, wherein z is the depth from the surface, and $\alpha$ is an optical absorption coefficient (also called "absorption coefficient") that depends on the composition of material present in the optically absorbing layer. In one embodiment, reflectance of the optically absorbing layer is measured across multiple regions that may be in different dies of a wafer or in different wafers. A difference in the reflectance measurement between two regions of the optically absorbing layer indicates nonuniformity in either thickness of the layer or absorptivity of the material in the layer (or both).

In one embodiment, the measurement is made on a planar area of dimensions larger than the heating and probing laser beams. In another embodiment, the measurement is made as a scan along a patterned line. The line width may be smaller than the laser beam diameter. In another embodiment, the measurement is made at either a fixed site or as a scan along a closely spaced array of patterned lines.

The above-described limit on the modulation frequency of the heating beam eliminates a thermal wave of the type described in U.S. Pat. No. 5,228,776 because the modulation frequency is sufficiently low to ensure that the temperature of the heated region varies in a substantially linear manner relative to the power of the heating beam (also referred to as "linear response condition"). For a predetermined modulation frequency, temperature of the above-described heated region changes as a function of the amount of energy absorbed therein, which in turn depends on the thickness of, and composition (e.g., the silicide phase) in the optically absorbing layer.

Also dependent on the thickness and composition is the sheet resistance of the optically absorbing layer. Therefore, because reflectance varies monotonically with temperature, the sheet resistance is related (in a monotonic manner, e.g. a one-to-one relation) to reflectance under linear response conditions which is an unexpected result. The apparatus and method of one embodiment use the just-described relationship between reflectance and sheet resistance to fabricate wafers, e.g. uniformity in reflectance of the optically absorbing layer is used as an indication of uniformity in sheet resistance.

Furthermore, for layers such as amorphized silicon or silicon germanium alloy (which has a low thermal conductivity compared to silicon), the response varies monotonically with layer thickness, a second unexpected result (note: here, the material property of the layer, such as resistivity or crystal phase may be constant, and only the thickness may vary). The just-described relationship between layer thickness and reflectance is used in another embodiment.

Specifically, in one embodiment, the apparatus and method use a substantially constant reflectance (e.g., constant to within a predetermined percentage, such as 1%) across multiple regions of a wafer to decide that the wafer has uniform sheet resistance in these regions, and therefore the wafer may be cleaned to be acceptable for further processing. When the measured reflectance is not constant across the wafer, further tests are performed as described below to determine which of one or more properties (such as sheet resistance and layer thickness) is nonuniform, and one or more parameters used in the fabrication process are changed to ensure that such properties of the wafers under fabrication become uniform.

In one embodiment, the above-described conductive layer includes one or more phases of silicide, and the absorption coefficient $\alpha x$ is related to the composition of phases of silicide that are present in the layer. For example, depending on annealing conditions, nickel can form any one or more of the following three crystalline phases: $Ni_2Si$, $NiSi$ or $NiSi_2$ each of which has a different absorption coefficient (the last-described phase $NiSi_2$ has the lowest resistivity and is preferred for certain integrated circuits). As another example, titanium silicide can form either of two crystalline phases, called C49 or C54 (again the last-described phase C54 has lower resistivity, and is preferred for certain integrated circuits). Therefore, a change in the reflectance measurement indicates a change in composition (e.g. in percentage of a given silicide phase).

In one embodiment, an optically absorbing layer's reflectance is measured by (1) focusing the heating beam on the patterned region, (2) modulating the power of the heating beam at a frequency that is predetermined to be sufficiently low to avoid creation of a thermal wave (e.g., by ensuring that temperature varies linearly relative to the modulated power) and (3) measuring the power (also called "reflected power") of a portion of another beam (also called "probe beam"), the portion being (a) reflected by the heated region, and (b) modulated in phase with modulation of the heating beam.

In this embodiment, the apparatus is calibrated ahead of time by relating measurements of the reflected power obtained in act (3) for a number of test wafers with corresponding measurements of surface resistance (based on a conventional method, such as four point probing). Thereafter, an acceptable range for the reflected power, that corresponds to an acceptable range for surface resistance (e.g., as indicated in the manufacturing specifications) is determined. Next, in an act (4), a reflected power measured for a production wafer is compared against the acceptable range for the reflected power, and if within the range, the production wafer is processed further in the normal manner (e.g., additional layers are formed).

In another embodiment, the temperature change is large (several degrees C.), and the reflectance measurement is done directly. Specifically, a DC heating beam (i.e. a heating beam of constant power) is applied and the reflected power is measured (1) either with and without the heating beam, or (2) measured first on a reference sample having a known reflectance, and then on the sample of interest to provide a measurement based on comparison. A difference in measurement solely due to heating is therefore measured. Another way to measure the temperature rise is by use of a thermal imager. The thermal imager could image a small field through a microscope to measure temperature at the point of heating.

If a measurement of the reflected power is outside the acceptable range, further tests are performed, to determine which of the attributes falls outside the manufacturing specifications. For example, a test wafer can be processed and measured with a four point probe. In another example, the above-described Rutherford backscattering method is used to determine the silicide phase as a function of depth in a test wafer associated with the production wafer. In either case, once the resistivity is known, the thickness of the optically absorbing layer is determined independently (e.g.

by use of Secondary Ion Mass Spectroscopy (SIMS)). Thereafter, thickness or resistivity or both are compared with ranges of acceptable values, to determine which property is affected. Based on the affected property, a corresponding process parameter is adjusted (e.g., annealing temperature is adjusted).

In one implementation, the above described acts (1)–(4) are repeated by the measurement apparatus between various acts normally performed in the fabrication of a substrate, at each of a number of regions of the optically absorbing layer. The out-of-range measurements (obtained as described above) are used to change one or more process parameters that control one of the fabrication acts (e.g., the annealing act) in a "feedback" loop to return the measurement to normal in the next wafer (or next batch of wafers). Performance of acts (1)–(4) during a fabrication process, without touching a substrate (i.e. in a non-contact manner) increases yield of the fabrication process, as compared to an off-line measurement of the resistance of a silicide layer on a test substrate. Also, performance of acts (1)–(4) as described herein indicates the efficacy of patterning of each individual production substrate that is otherwise not measurable e.g., when using an unpatterned substrate (such as a test substrate).

A reflectance measurement as described herein can be performed at any time relative to etching. Reflectance measurement after etching takes into account effects on surface resistivity of the dimensions of a patterned region (e.g., a contact for a polysilicon gate or a contact for a source or drain region of a field effect transistor) formed during etching. Therefore, in one implementation, the measurement is performed over a patterned region that is smaller in size (e.g., an order of magnitude smaller) than a spot size of the probe beam. In one example, the patterned region has a diameter of approximately 0.2 μm, whereas the spot size has a diameter that is ten times larger in this example, such as 2 μm. If more than one feature (such as a trace which is also called "line") is illuminated by the probe beam, the measurement is an average measure of reflectance of all features that are illuminated. Note that the just-described method can be used to increase sensitivity to conductive silicide lines by use of beams polarized along the direction of the conducting lines as described in the U.S. patent application, Ser. No. 09/521,232 that was incorporated by reference above. In this manner, fine patterned lines may be measured, where the pitch of the conducting lines is less than the wavelength of the probe beam.

In this implementation, the absorption coefficient a of the silicide is several orders of magnitude (e.g., three orders) greater than the absorption coefficient of the underlying layer (e.g., doped silicon). So, individual features of the silicide layer in the spot formed by the probe beam are at a higher temperature than the surrounding regions, and a signal reflected by the features (which may be an order of magnitude or more smaller in area than the area of the probe beam's spot) is detected by the apparatus even in the presence of additional signals reflected by the regions surrounding the individual features (e.g., by use of a lock-in amplifier as described below). Thus, effects on surface resistance of the etched pattern (such as dependence of the phase of titanium silicide on the width of the traces) can be identified, in a manner that was previously not possible, e.g., by use of four point probes. Additional methods, such as those described in the above-referenced application, Ser. No. 09/521,232 can take advantage of the polarization of a probing beam (by, for example, polarizing the probing beam along the length of the lines) to further increase discrimination between the heated lines and the background substrate.

DETAILED DESCRIPTION

Figure 1A:
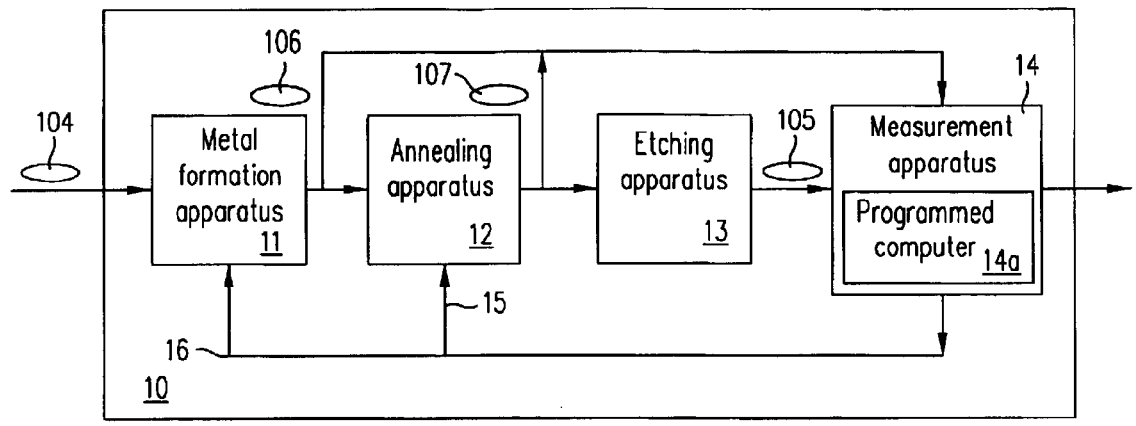
FIG. 1A illustrates, in a block diagram, use of one embodiment of a measurement apparatus of this invention with a metal formation apparatus for forming a conductive layer and a metal etching apparatus for patterning the conductive layer.

A processing unit 10 (FIG. 1A) can be operated in accordance with the invention to create integrated circuit (abbreviated as "IC") dice by processing a substrate 104 to form a patterned substrate 105, measuring the resistance of one or more conductive lines in patterned substrate 105, and adjusting the processing in real time if necessary. Specifically, unit 10 includes a metal formation apparatus 11 that forms on substrate 104 a layer 103 (FIG. 1B) of conductive material (such as a metal) to form a metalized wafer 106. The deposited layer has a thickness t (FIG. 1C) of, for example, 100 angstroms (in another example 300 angstroms).

Next, wafer 106 is heated in an annealing apparatus 12 (such as a rapid thermal processor) to form a metal silicide (at an interface in wafer 106 where the metal contacts silicon). Next, the metal in wafer 107 that remains unreacted is removed, e.g., by selective etching in etching apparatus 13, e.g., to form one or more conductive pads in substrate 105. Processing unit 10 also includes a measurement apparatus 14 that measures reflectance of the silicide on patterned substrate 105, or of one or more regions on unpatterned substrate 103 or both (i.e. before and after patterning of the same substrate).

In one embodiment of apparatus 14 includes an optional programmed computer 14A that drives an active signal on line 15 that is coupled to annealing apparatus 12, or on line 16 that is coupled to metal formation apparatus 11, or both, depending on the measurement. A change in the process parameter can be determined automatically by software in programmed computer 14A, or can be entered by a human operator.

In one embodiment, substrate 106 having a metal layer is transferred directly to measurement apparatus 14 for measurement of a property of the metal layer. An example of such a property is reflectance (that is used as an indication of sheet resistance as described herein). Such a measurement subsequent to metal formation and prior to annealing provides a more immediate feedback to control the operation of metal formation apparatus 11, as compared to an otherwise long delay (several hours or days) between forming a conductive layer and etching a pattern.

Measurement apparatus 14 determines, between acts of fabricating unpatterned substrate 104 or patterned substrate 105 (FIG. 1B), a measure of sheet resistance in the following manner by use of two beams 101 and 102 of electromagnetic radiation (such as laser beams). A first beam (also called "heating beam") 101 has a power (also called "heating power") that is modulated at a predetermined frequency. In one example, beam 101 has a wavelength of 0.83 microns, has an average power of 10 milliwatts, a diameter of 2 microns and is modulated at 450 Hertz.

A second beam (also called "probe beam") 102 has constant power also incident on region 103R. In the above-described example, beam 102 has a wavelength of 0.98 microns, a power of 10 mW and a diameter that is equal to or smaller than the diameter of beam 101 (e.g., 2 microns). First beam 101 is incident on and heats region 103R of an optically absorbing layer 103 (that may be a conductive layer on substrate 104 or a silicide layer on substrate 105 or may be a silicide layer formed in polysilicon, with an intervening insulator layer (such as silicon dioxide) between substrate 105 and the polysicon layer) to a temperature T. Second beam 102 is reflected by region 103R in phase with modulation of first beam 101, because temperature T (and therefore the reflectance) is modulated in phase with modulation of first beam 101 (under linear response conditions).

The predetermined frequency of modulation of first beam 101 is selected to be sufficiently small to ensure that at any time the temperature of optically absorbing layer 103 is approximately equal to (e.g., within 90% of) the temperature of optically absorbing layer 103 when heated by an unmodulated beam (i.e. a beam having constant power, equal to the instantaneous power of the modulated beam). For example, the modulation can be sinusoidal between 0 and 50 milliwatts, i.e. P=50 sin (2πft), in milliwatts, where f is the modulation frequency. In such an example, at the time when the modulated power has an instantaneous value of 25 mW, the temperature under the heating beam approximately equals (e.g., is no less than 90% of) the temperature obtained with a heating beam having constant power, e.g., 25 mW.

In one embodiment, the predetermined frequency is selected to cause all locations in region 103R illuminated by probe beam 102 to be at substantially same temperature (e.g., varying less than 10%). Such a linear response condition occurs when the thermal wavelength λ is at least an order of magnitude larger than the radius of probe beam 102 (which may be, for example, 1 micron as discussed above). As discussed more completely below, under the linear response conditions, thermal wavelength λ is given by $$\lambda = \sqrt{\frac{k}{2\pi f \rho c}} \qquad (1)$$

where k is the thermal conductivity of the silicon substrate, ρ is the density, c is the specific heat, and f is the frequency of modulation of heating beam 101. For silicon, with k=1.5 W/cm-° K, ρ=2.33 g/cm$^3$, c=0.7 joule/g-° K, with a probe beam radius of 1 μm, a wavelength of 100 μm is obtained at a frequency f of 15 kHz. This wavelength is two orders of magnitude greater than the probe beam radius, ensuring linear response conditions over the region of measurement.

Figure 2A:
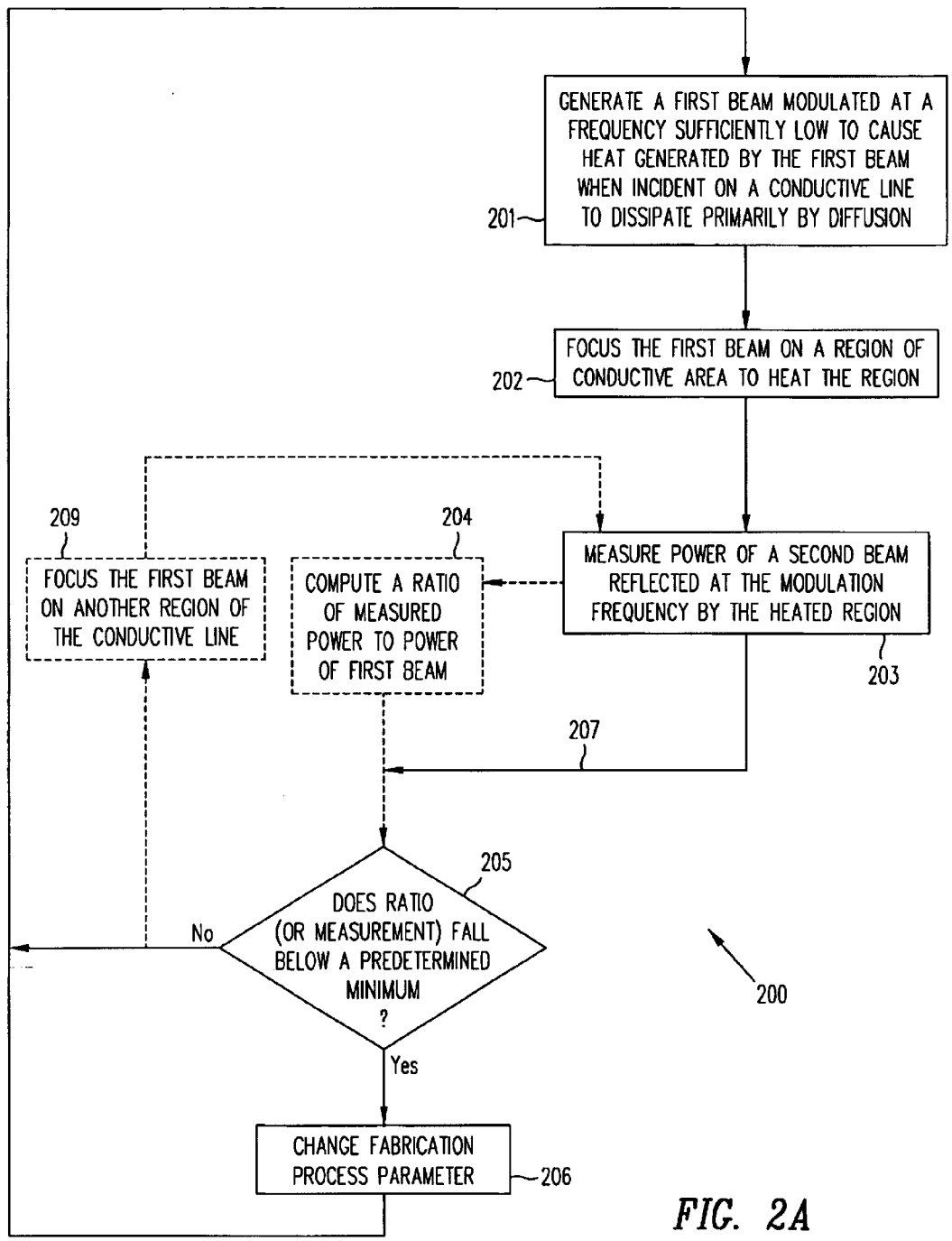
FIGS. 2A and 2B illustrate, in flow diagrams, two embodiments of a method for using the beams of FIG. 1B to measure a change in resistance of silicide layer, and use of the measurement to control the processing of wafers by the metal formation apparatus and metal etching apparatus in FIG. 1A.

Such a linear response in temperature of optically absorbing layer 103 to incidence of modulated beam 101 allows the use of a linear solution to the heat transfer equation 2 described below, thereby to allow electrical and thermal conductivity to be related to one another as described in reference to method 200 (FIG. 2A). Therefore, the predetermined frequency f is selected to be lower than a maximum frequency beyond which nonlinearities in temperature response of exposed region 103R become noticeable.

Figure 1B:
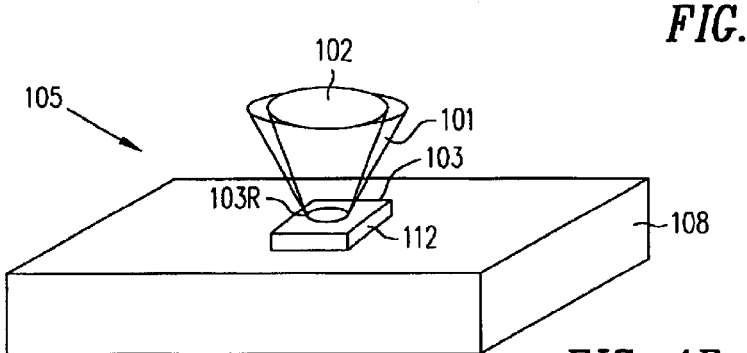
FIG. 1B illustrates, in the apparatus of FIG. 1A, a heating beam 101 focused on a region 103R of an optically absorbing layer 103 under steady state conditions while a probe beam 102 is used to measure reflectance of region 103R.
Figure 1C:
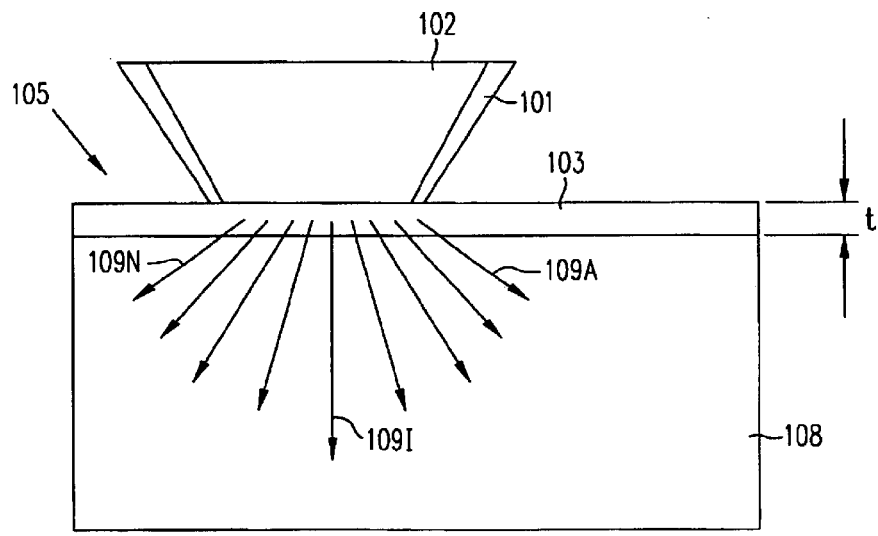
FIG. 1C illustrates, in a cross-sectional diagram, generation of heat by beam 101, diffusion of heat from optically absorbing layer 103 (of thickness "t") into underlying layer 108 as illustrated by arrows 109A–109N.
Figure 1D:
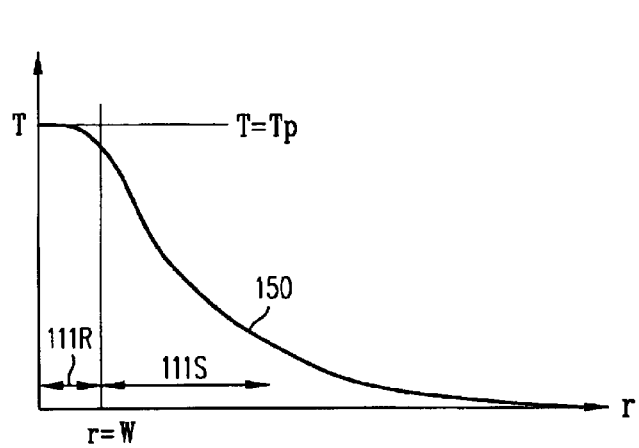
FIGS. 1D and 1E illustrate, in graphs, temperature as a function of radial distance r and as a function of depth z from heated region 103R illustrated in FIG. 1B.
Figure 1E:
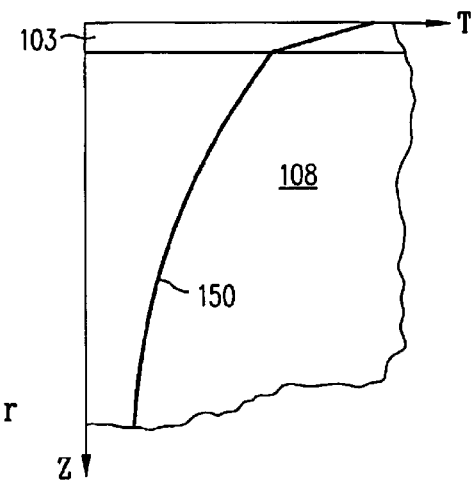
Figure 1F:
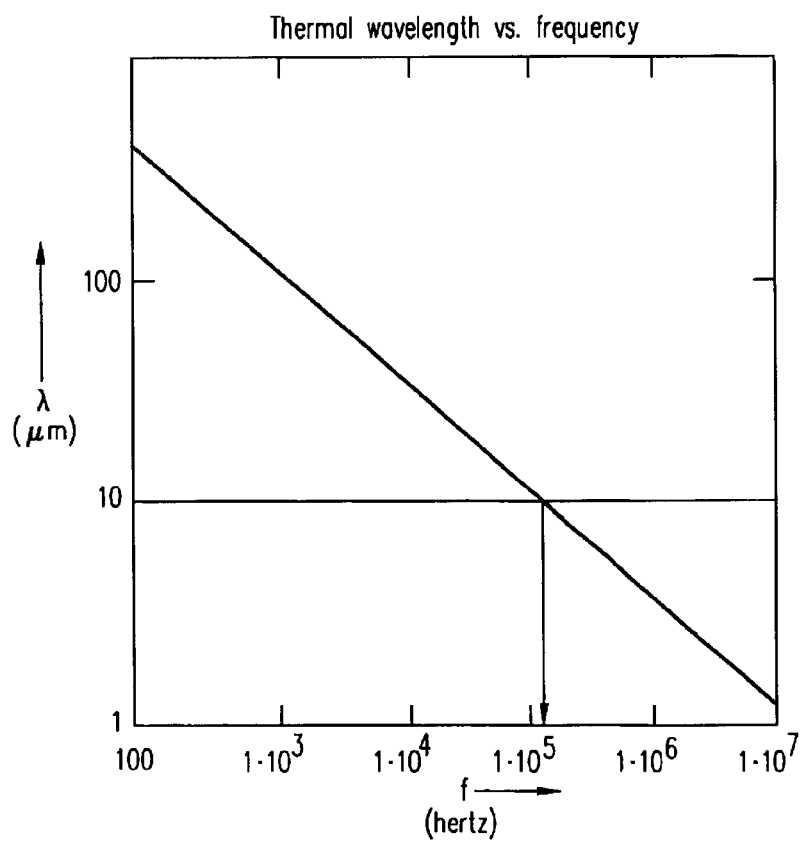
FIG. 1F illustrates, in a graph, the modulation frequency as a function of thermal wavelength.

So, a maximum limit on the predetermined frequency is inversely related to a diameter of probe beam 102, as described above in reference to equation 1. FIG. 1F illustrates thermal wavelength λ as a function of modulation frequency f. A 90% criterion for a probe beam of 1 micron radius is met at a modulation frequency of 100 kHz.

Therefore, frequency f of modulation of heating beam 101 is kept low enough to prevent generation of any thermal waves. Such avoidance of thermal waves allows a static temperature distribution to form in layer 103, with a peak at the point where beam 101 illuminates the surface of layer 103. In the presence of thermal waves, the temperature distribution is not well defined, potentially increasing the difficulty of correlating the reflection signal to the temperature distribution (in order to correlate the measured reflection signal to silicide phase and thickness). The frequency criterion set forth in equation (1) above is established approximately by solving the following equation for heat transfer from region 103R:

$$\ddot{v} + \left[\frac{q}{k} - j\omega\frac{\rho c}{k}\right]v = 0 \qquad (2)$$

where the double dot notation indicates the second derivative with respect to distance. v is the difference between the temperature and the ambient temperature, q is the heat per unit volume generated by absorption of the laser beam, k is the thermal conductivity, r is the density, and c is the specific heat, and ω=2πf is the modulation frequency, where f is the modulation frequency in Hertz.

Note that the discussion herein makes a specific reference to a conductive region 103R, although a similar analysis in applicable to other portions of conductive layer 103 (such as a line). Moreover, although the following description refers to a wafer of silicon (such as wafer 103, 104, or 105), the description is equally applicable to any substrate that supports a conductive layer, and other examples of such a substrate include a glass plate and a resin core. For convenience, the same reference numerals are used for a wafer and a substrate.

The diffusion of heat from region 103R creates a temperature profile 150 (FIGS. 1E and 1D) in layer 108 beneath region 103R, with a hottest point (having a peak temperature $T_p$) located at the center of region 103R. In one example, conductive region 103R is supported on an underlying layer 108 (FIG. 1B) of a wafer 105 having a thermal conductivity Kc that is almost the same as the thermal conductivity $K_m$ of conductive region 103R. Note that such an equality in thermal conductivities is not required for the relation in equation 1 described above. Instead, equation 1 holds as long as the thermal conductivity Kc of layer 108 is greater than the thermal conductivity Km of region 103R.

In one embodiment, the layer being evaluated is optically absorbing (partially transparent), and laser light absorption is a function of two parameters: (1) the optical absorption co-efficient and (2) the thickness. The optical absorption co-efficient is a function of the crystal and material properties (and hence relates to the conductance for conductive films, such as silicides, which have various phases, and one of these phases may be preferred because of its lower resistivity). Therefore, the temperature relates to the sheet resistance, which is the ratio of the conductivity to thickness. Note that this works for optically absorbing (semi-transparent) layers. However, when the layer being evaluated is opaque, the absorption is independent of thickness.

Temperature profile 150 has substantially the same "bell" shape (FIG. 1D) at any time during a cycle at the predetermined frequency. Therefore, temperature T is modulated without forming a wave in space (in a manner analogous to direct current ("DC")) during the cycle. Temperature T is modulated in accordance with this invention to increase the accuracy in measurement of sheet resistance. Use of a lock-in amplifier obtains a high signal-to-noise ratio (as compared to not using the lock-in amplifier), because noise changes as the square root of the bandwidth of the lock-in amplifier. Therefore, in one embodiment, a lock-in amplifier is used for synchronous detection of a portion of probe beam 102 reflected by region 103R. Moreover, the predetermined frequency can be arbitrarily low, limited only by the minimum throughput required of the fabrication process.

Note that the temperature at the peak is a function of the thickness of conductive layer 103, as long as conductive layer 103 is semi-transparent (i.e. optically absorbing). The thicker the conductive layer 103, the greater the absorption, and, hence, the greater the heat generation in the layer 103. Therefore, this is an example of a measurement where the measured property—the temperature—correlates to the thickness of layer 103 (when calibrated with samples having known values). Since the thickness t determines the sheet resistance Rs if the resistivity is kept constant (Rs=r/t, where r is the resistivity), the measurement made by apparatus 14 (FIG. 1) is correlated to sheet resistance (by calibration). In general, any measurement that is sensitive to the thickness t correlates to the sheet resistance. Therefore, a method of the type described herein uses a layer's thickness measurement to measure sheet resistance.

Such a measurement is applicable to a number of structures commonly found in integrated circuits. For example, gate conductors consisting of narrow polysilicon lines with cobalt or nickel silicide are formed in the polysilicon, and such lines are separated from the silicon substrate by a thin layer (e.g. less than 20 angstroms in the transistor, and several hundred to a thousand angstroms outside the transistor) of an insulator, such as silicon dioxide. In such a case, a series of measurements may be made along the length of the line to determine the absolute value of resistivity, as well as variation in resistivity. In another example, cobalt or nickel silicide is used to contact the transistor source and drain structures, and a measurement may be made to determine the integrity of the contact.

In one embodiment, a measure of the sheet resistance of region 103R is determined by performing acts 201–206 of a method 200 (FIG. 2A). Specifically, in act 202, heating beam 101 is focused on a region 103R (FIG. 1B) of a semiconductor wafer 105 that has been coated with a film of metal (such as nickel), and annealed in a rapid thermal processor for a predetermined time period at a predetermined temperature (such as 30 seconds at 500° C.). The predetermined time period and predetermined temperature are part of a process for manufacturing integrated circuit dice. In act 201 (FIG. 2A), the power of heating beam 101 is modulated at the predetermined frequency. Note that acts 201 and 202 can be performed in reverse order, i.e. act 202 performed first followed by performance of act 201.

Next, the power (also called "reflected power") of probe beam 102 after reflection by region 103R is measured in act 203. Note that a narrow band filter or a lock-in amplifier (described below) may be used to obtain the just-described measurement. Thereafter, in act 204, the reflected power is directly compared with power measured during calibration of a test wafer having a known sheet resistance.

Figure 3:
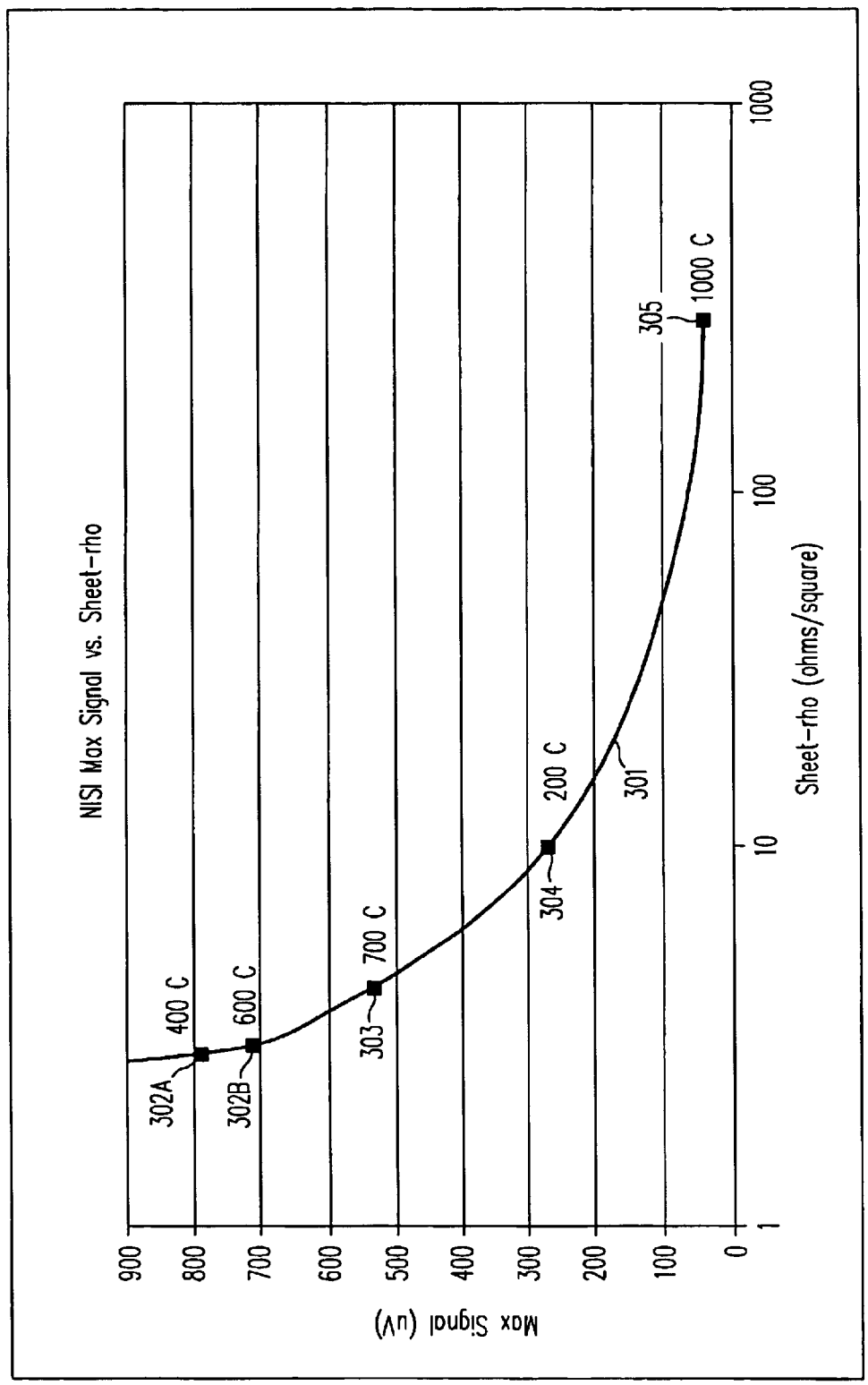
FIG. 3 illustrates, in a graph, a change in reflectance (plotted along y axis after scaling by a factor of 1000) of silicide layer as a function of sheet resistance of the conductive layer.

During calibration, the just-described acts 201–203 are performed for each of a number of test wafers, and sheet resistance of these test wafers is determined by a well known method, such as four point probing, and thereafter these results are plotted in a graph as illustrated in FIG. 3. Specifically, FIG. 3 illustrates a scatter plot comparing the measured resistance (X-axis) with the measured reflection signal (Y-axis). A line 301 (also called "correlation line") correlates the points on the graph to one another, and illustrates the relationship between sheet resistance and measured reflectance.

Specifically, line 301 is drawn through points 302A, 302B and 303–305, and provides an empirical relation between the reflectance measurement and sheet resistance. Note that instead of graphically drawing line 401, an equation can be fitted to points 302A, 302B and 303–305 (e.g., the constants in a second order equation can be determined from the coordinates of these points). In the example illustrated in FIG. 3, points 302A and 302B were found (by use of a prior art method) to be generated by test wafers that have the crystalline phase $NiSi_2$ whereas point 303 was generated by a test wafer having the crystalline phase NiSi. Similarly, points 304 and 305 were generated by test wafers having phase $Ni_2Si$. Therefore, the correlation shown by line 301 indicates a theoretical basis (discussed below) for use of reflectance as a resistance measure.

Line 301 indicates anneal temperature dependence of the reflectance measurement, which dependence can arise from a number of physical causes. Specifically, the optical absorption coefficient of the material (such as one or more silicides) in layer 103 is a function of temperature. Moreover stresses in layer 103, and at the interface between layers 103 and 108 are a function of temperature. Moreover, there are reflection components both from the front surface of layer 103, and from the interface between layers 103 and 108. These reflection components interfere with one another, and the interference is a function of the stress. The stress can cause birefringence, leading to a change in polarization of one of the reflected components relative to another. The detailed nature of the just-described dependence is not critical for method 200; instead, method 200 uses merely the existence of such a dependence (which is a monotonic function of temperature over the temperature range of measurement).

Phase $NiSi_2$ has the lowest resistance, and is preferred in this example. As noted above, sheet resistance and reflectance are both functions of the crystalline phase and thickness, and are therefore related as illustrated by line 301 in FIG. 3. In one example, sheet resistance of layer 103 needs to be less than 5 ohms/square, and in this example the reflectance measurement must exceed 500 microvolts. Therefore, in the example if the reflectance measurement in act 203 for a production wafer does exceed 500 microvolts, then the production wafer is processed further in the normal manner. If the measurement falls outside the specifications (e.g., below the predetermined minimum of 500 microvolts) for any of substrates 104–106, a process parameter is adjusted by apparatus 14.

Figure 2B:
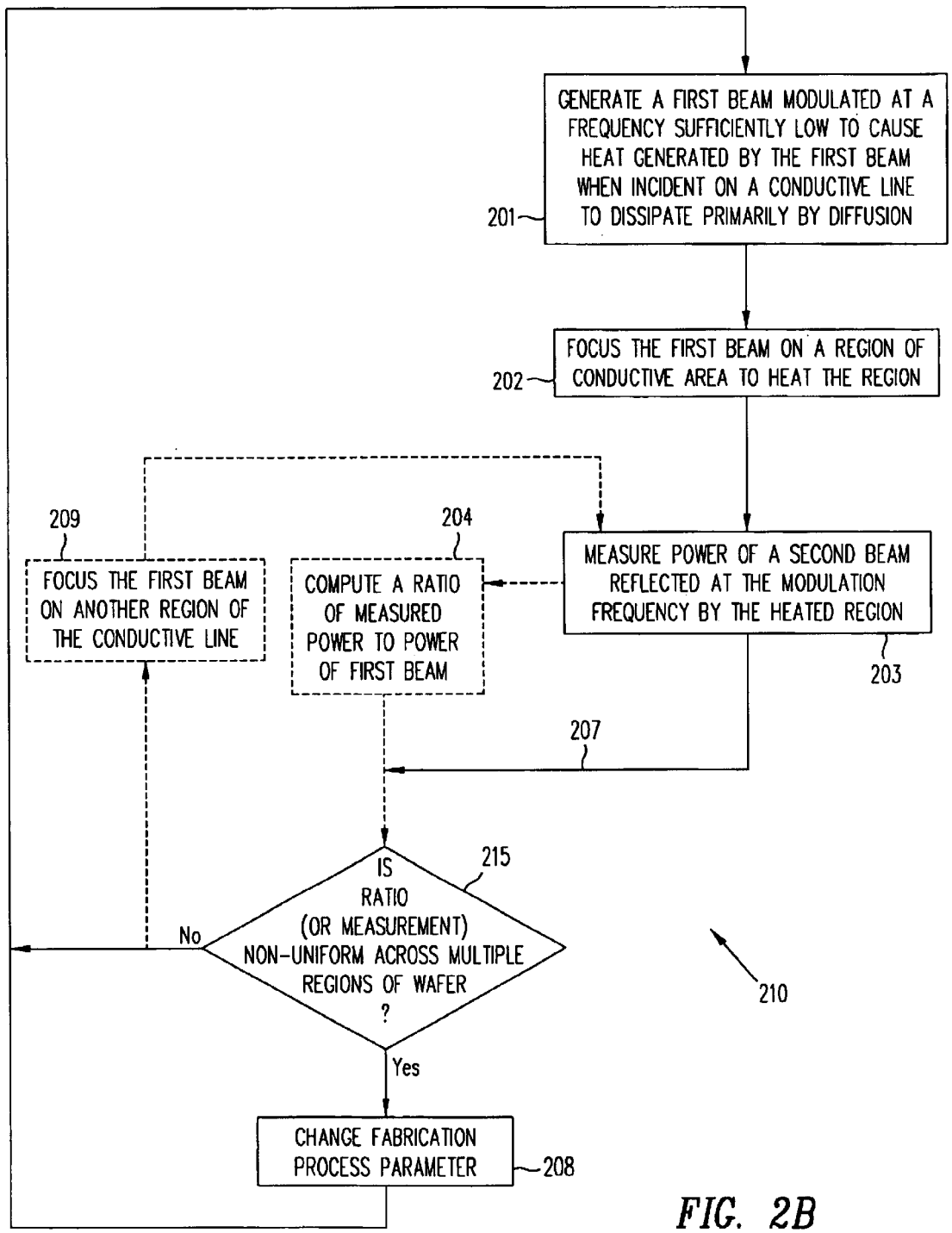

In another embodiment, a method 210 (FIG. 2B) uses a substantially constant reflectance (e.g., constant to within a predetermined percentage, such as 1%) across all regions of a wafer to decide that the wafer under evaluation has uniform sheet resistance. Similarly, constant reflectance measurements are done along the length of a silicided polysilicon gate line at measurement intervals on the order of the beam radius (1 µm) to determine the uniformity of resistance along the length of the line (note that the line width can be smaller than the beam diameter).

Specifically, in this embodiment, method 210 compares (in act 215) the measured reflectance in region 103R with the corresponding measured reflectance in another region, and if the two measurements differ by more than a predetermined percentage (e.g., 10%), computer 14a (FIG. 1A) goes to act 208 to change a process parameter used in fabrication. If measurements in two (or more) regions of a substrate are uniform (differ by less than the predetermined percentage), then the production wafer is processed further in the normal manner, and computer 14a goes to act 201 to evaluate another production wafer.

In one embodiment, if the measurements are non-uniform (or if a measurement falls below the predetermined minimum) processing of wafers in annealing apparatus 12 is halted until the cause of the problem is found. Diagnosis may involve the use of other techniques, such as microscopic examination, Rutherford backscattering, or evaluation of the processing equipment. Once the cause of the problem is found and fixed, processing of additional wafers resumes.

Instead of using the signal value directly, a ratio of the reflected power to the power of heating beam 101 is computed in yet another embodiment. The ratio indicates a measure of sheet resistance of conductive region 103R. Note that during the just-described operations, the power (also called "probe power") of probe beam 102 that is incident on region 103R remains constant in this embodiment. The ratio may itself be compared (in act 205) with a predetermined limit to check if sheet resistance of region 103R is within specifications and if so, return to act 201 (for another wafer).

The ratio (also called "steady-state ratio"), when multiplied by a predetermined constant yields, per unit area, the sheet resistance of conductive region 103R. The value of such a determined constant can be found empirically, or by an analytical method. As described more completely below, the predetermined constant's value is determined by a number of factors, such as absolute reflectance $R_o$ of the conductive region 103R in heated region 111R, dielectric constant of free space $\in_0$, frequency of modulation $v_L$ of the reflected portion of probe beam 102, Boltzmann's constant $k_B$, electron charge q, ambient temperature $T_o$, rate of change of resistivity with temperature, and power of probe beam 102, as well as the thickness $h_i$ and thermal conductivity Kc of silicide layer located underneath the conductive region 103R. The steady-state ratio when multiplied by such a predetermined constant yields the sheet resistance ($\rho_e/h_m$) where $\rho_e$ is the resistivity, and $h_m$ is the thickness of conductive region 103R. Note that the absorption constant α varies inversely with resistivity—a low resistivity layer has a short absorption length and, therefore, a higher absorption constant, as compared to a layer having higher resistivity. Therefore, the steady-state-ratio actually equals a constant times the inverse of the sheet resistance, as shown below.

The temperature of region 103R may be found by solving the heat diffusion equation, $$\frac{\partial^2 T}{\partial r^2} + \frac{2}{r}\frac{\partial T}{\partial r} - \frac{\rho C}{K}\frac{\partial T}{\partial t} + \frac{A}{K} = 0$$

where ρ is the density, C is the specific heat, K is the thermal conductivity, and A is the internal heat generation per unit volume.

The general solution is $$T(r) = \frac{P}{2\pi w_0 K \left(1 + j + \frac{\lambda}{w_0}\right)} \frac{\lambda}{r} e^{-(1+j)\frac{(r-w_0)}{\lambda}}$$

where P is the heat flux generated by the illumination of the silicide (the laser power absorbed and converted to heat in the silicide layer). This is $$P = P_{gen}(1 - e^{-\alpha h})$$

where α is the absorption constant of the silicide layer (the inverse of the absorption length), $P_{gen}$ is the generation laser power, and h is the layer thickness.

The wavelength is given by $$\lambda = \sqrt{\frac{K}{\omega \rho C}}$$

as above. For silicon at 1 kHz the wavelength is 119 µm, more than two orders of magnitude than the spot radius of 1 µm. Therefore, $w_o \ll \lambda$, and the temperature relationship simplifies to $$T(r) = \frac{P}{2\pi r K}$$

Assuming the reflectance varies linearly over the range of measurement because the temperature rise is small, the reflectance is given by $$R = R_o + R_1 T$$

The signal in terms of the probe and heating laser power is given by evaluating the temperature at the edge of region 103R ($r = w_o$) and applying the above relation to calculate the reflected signal power $$P_{sig} = R_1 T(w_0) P_{probe} = \frac{P}{2\pi w_0 K} R_1 P_{probe}$$

From this relationship, the steady state ratio is given by $$\frac{P_{sig}}{P} = \frac{R_1 P_{probe}(1 - e^{-\alpha h})}{2\pi w_0 K} \approx \frac{R_1 P_{probe} \alpha h}{2\pi w_0 K}$$

where the last relation holds when the product $\alpha h \ll 1$ (wherein "$\ll$" denotes at least an order of magnitude smaller). Such an assumption is made to simplify the above equation for descriptive purposes; nevertheless, in accordance with the invention, a relationship to absorption length and film thickness for the case of ($\alpha h$ is on the order of unity. Note that when $\alpha h$ is on the order of 2 (e.g. 10% transmission), the layer ceases to be semi-transparent, and becomes opaque. Under these conditions, sensitivity to $\alpha h$ is lost. The steady state ratio is a function of the temperature dependence of reflectance, the absorption length, layer thickness, spot diameter, probe laser power, and thermal conductivity of the substrate layer.

In one implementation, heating beam 101 is focused (in act 209) in another region and the measurement is repeated (in act 203), and the two measurements are compared. Any change in thickness $h_m$ or phase of silicide results in a change in the steady-state ratio that can be detected by the comparison. In another implementation, the above-described measurements (either a single measurement or two or more measurements per region) are repeated after focusing (see act 210) heating beam 101 in each of three different regions. Also, instead of comparing numerical measurements, a change in the steady state ratio can be detected by plotting a graph of the steady state ratio as a function of distance.

Therefore, the event of a change in the steady-state ratio (e.g., exceeding a predetermined limit) provides an indication that the fabrication process has changed, and that conductive region 103R is no longer within the specification. In response to the indication, an operator or an appropriately programmed computer changes a process parameter that controls the fabrication of layer 103 (see act 208 in FIG. 2A), and that changes the process to return a conductive line in the next wafer to within the specification.

For example, the operator identifies a source of contamination in metal formation apparatus 11 (FIG. 1A) that degrades the resistivity of a metal layer formed on wafer 103, and changes a parameter related to the source. As another example, the operator decreases the annealing temperature from 700° C. to 400° C. to increase the formation of $NiSi_2$ (relative to other phases being formed therein), thereby to decrease the sheet resistance.

A steady-state ratio as described above is measured at a single spot (e.g., in region 103R), allowing the measurement (of the value of reflected power) to be made in a more compact area (e.g., a region of length 1 micron) than possible by a method that requires two locations (each displaced from the other), e.g., as disclosed in U.S. Pat. No. 5,228,776. In the just-described example, since only the power of beam 101 that is incident on layer 103 heats region 103R, width W (FIG. 1B) of region 103R can be smaller than the diameter of beam 101 (that may have a minimum size larger than line width W). The temperature of a region 103R (of width equal to the diameter of beam 101) that is heated under linear response conditions as described herein is a function of the thermal properties of thickness and material composition in heated region 111R.

Note that a conductive region (e.g. formed of silicide lines) is much more conductive than the substrate (e.g. formed of silicon), so that polarization of heating beam 101 along the length of the lines causes the heat to be more likely to be absorbed in the lines. Also, polarization of the measurement beam 102 along the lines makes the reflection of that beam to be more likely from the lines. Consequently, the sensitivity of the measurement is to the lines rather than to surrounding material. The use of polarization is described in greater detail in the related application, Ser. No. 09/521,232 that was incorporated by reference above.

Since the silicide lines are much more conductive than the silicon substrate, polarization of a beam along the length of the lines causes the incident heat to be absorbed by the silicide lines. Also, polarization of a measurement beam along the lines makes reflection of that beam come preferrably from the metal lines. Consequently, sensitivity of the measure is tailored to the patterned lines, rather than to any surrounding material.

In the prior art (e.g., U.S. Pat. No. 5,228,776), the heat propagates away from a heated region in a thermal wave, and the temperature at the heated region is not a direct function of the physical properties of the conductive region. This is because a thermal wave at any point is the sum of heat from an outgoing wave and heat from waves reflected from one or more regions in the line where the metal properties have changed. This sum is difficult to quantify in the prior art, because the reflective properties of defects may not be known in advance.

In contrast, under linear response conditions, the heat at any point is affected in a quantifiable manner by the reflective properties of defects or vias at a distance from the point. Also, method 200 provides an unexpected result, specifically the value of reflected power as measured by method 200 is unaffected by the presence of non-flat surfaces (that cause problems in the prior art, e.g., U.S. Pat. No. 5,228,776) because a reflectance measurement as described herein is independent of the small angular deflection that is caused by periodic undulation of a surface by passage of a thermal wave. In addition, silicides often have relatively rough surfaces, whose roughness is a function of the crystal phase (causing changes in grain size). This roughness can be on the order of 0.1 $\mu$m. However, such roughness does not affect a measurement in an embodiment described herein because the wavelength is very long (as compared to U.S. Pat. No. 5,228,776), and so scatter is negligible (because the roughness features are small compared to the wavelength).

In one example, apparatus 14 operates heating beam 101 at 0.01 watts as measured at the plane of the substrate 108 and obtains intensity measurements as follows: probe beam has an incident power on heated region 103R of 10 milliwatts, and a modulated component of reflected power of 0.5 microwatts, at 0.01 watts of heating beam power compute $\Delta P/P$ as $(0.5 \times 10^{-6}/0.01) = 0.5 \times 10^{-4}$ assuming that the $\Delta P$ is zero when P is zero. Next, in act 205, the just-described ratio is compared with a predetermined minimum (e.g., $0.4 \times 10^{-4}$), and if the ratio is smaller than the minimum then a process parameter is changed in act 206.

In an alternative embodiment, instead of performing act 204, a branch 207 from act 203 goes directly to act 205, if the power of heating beam 101 is the same as the power used during calibration. Therefore, in the alternative embodiment, a measurement of the modulated component of the reflected probe beam is used directly as a measure, per unit area, of the electrical resistance of the conductive region 103R in act 208.

Use of steady-state conditions as described herein eliminates the need for a generation beam having the high modulation frequency required by U.S. Pat. No. 5,228,776 to set up a thermal wave. Specifically, the above-described method eliminates the need to generate a beam modulated at a frequency in the range of 1 MHz to 100 MHz, and instead requires a beam modulated at a frequency that is several orders of magnitude smaller, e.g., in the range of 0.01 kHz to 100 kHz, thereby eliminating the thermal wave in the region 103R (because a method in accordance with the invention uses a frequency so low that over the dimensions of the region of measurement that the solution closely approximates the DC case (modulation frequency=0), where no wave exists.

Figure 4:
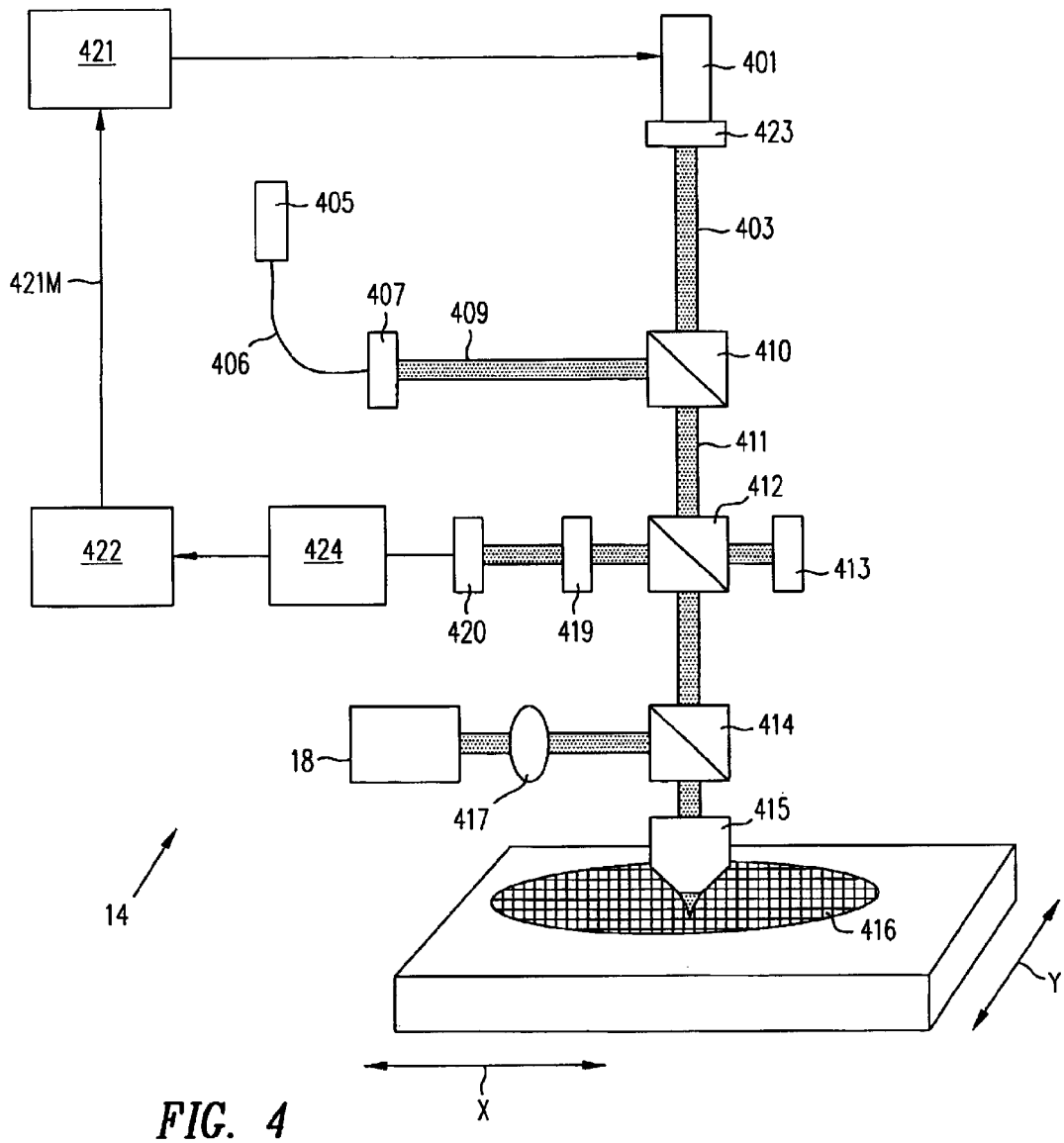
FIGS. 4 and 5 illustrate, in block diagrams, two embodiments of a measurement apparatus, each of which can perform either of the methods illustrated in FIGS. 2A and 2B.

Acts 201–207 and 215 of method 200 or 210 can be performed by use of a sheet resistance measurement apparatus 14 (FIG. 4) having two lasers that create the two beams 101 and 102. Specifically, apparatus 14 includes a laser 401 for creating a beam 101 of electromagnetic radiation at a predetermined wavelength, such as infrared light, ultraviolet light, X-rays, gamma rays, or radiation in the microwave or radio frequencies. In a preferred embodiment, laser 401 is an AlGaAs diode laser that emits electromagnetic radiation of wavelength 830 nm (available from, for example, Spectra Diode Labs, of San Jose, Calif.).

The electromagnetic radiation created by laser 401 is transmitted to a collimator 423 to create heating beam 101 of a predetermined diameter (e.g., 5 mm). In one implementation, heating beam 101 has a maximum power of, for example, 100 milliwatts, although the power is modulated at a predetermined frequency (e.g., 2000 Hz) by a laser driver 421. Laser driver 421 receives an oscillator output from lock-in amplifier 422.

Apparatus 14 further includes a second laser 405 that creates a beam 102 of electromagnetic radiation used to measure a change in reflectance of region 103R (FIG. 1B) in response to change in power of heating beam 101. In one implementation, laser 405 is an InGaAs diode laser (available from, for example, Spectra Diode Labs, San Jose, Calif.) that emits electromagnetic radiation of wavelength 980 nm. The electromagnetic radiation created by laser 405 is transferred by an optical fiber 406 to another collimator 407 also included in apparatus 14.

Collimator 407 emits probe beam 102 having a predetermined diameter that is identical to or smaller than the predetermined diameter of beam 101. Moreover, probe beam 102 has a maximum power of, for example, 7 milliwatts. Therefore, the power of probe beam 102 is an order of magnitude smaller than the power of heating beam 101, so that conductive region 103R is not noticeably heated by probe beam 102 (i.e. not enough to affect the empirical relation between reflectance and sheet resistance that is present under linear response conditions).

Apparatus 14 also includes a dichroic beam splitter 410 that combines heating beam 101 and probe beam 102 to form a combined beam 411. Combined beam 411 passes through beam splitters 412 and 414 (that are also included in apparatus 14) to an objective lens 415. Beam splitter 412 passes half of the combined beam 411 to photodiode 413 (e.g., a Si/Ge photodiode stack made by EG&G) that monitors the forward power in both beams 101 and 102.

Objective lens 415 can be, for example, a 0.9 NA, 100× objective lens available from Nikon of Yokohama, Japan. The focal planes of beams 101 and 102 are offset from each other along the optical axis due to the chromatic response of lens 415. For example, in region 103R (FIG. 1B) the diameter of heating beam 101 is slightly larger than the diameter of probe beam 102. Therefore, the system is operated with region 103R at the focal plane of probe beam 102, so that the spot formed by beam 102 falls within the spot formed by beam 101.

As noted above, a portion of combined beam 411 is deflected to a photodetector 413, such as part number J16-8SP-RO5m-HS from EG&G Judson of Montgomeryville, Pa., USA. Photodetector 413 is used to measure the incident power of one or both of beams 101 and 102.

Light reflected from wafer 105 passes back through objective lens 415 and through beam splitter 412. Beam splitter 412 sends 50% of the reflected light through a filter 419 to a photodetector 420. Filter 419 is a narrow band filter (e.g., available from Corion, Inc.) that removes the reflected portion of heating beam 403 while passing the reflected portion of probe beam 409 to detector 420. Thereafter, photodetector 420 senses the intensity of the reflected portion of probe beam 409, and passes a voltage signal to amplifier 424.

Amplifier 424 converts the voltage signal into a current signal and passes the current signal to a lock-in amplifier 422. Lock-in amplifier 422 includes an oscillator as a frequency source that is used to detect the power of the reflected portion of probe beam 102 modulated at the predetermined frequency. The frequency source in lock-in amplifier 422 also provides a frequency signal on a line 421M to a laser driver 421. Laser driver 421 uses the frequency signal on line 421M to drive laser 401 at the predetermined frequency that is sufficiently low to modulate the amplitude of heating beam 403 to ensure heat transfer by diffusion as described herein.

Amplifier 424 also includes a low pass filter to measure the dc component of the output of photodiode 420, corresponding to the dc amplitude of the reflected laser beam 409. This signal may be used to create the aforementioned steady-state ratio, which is the ratio of the ac signal as measured with lock-in amplifier 422 to the dc signal as measured with the low-pass filtered signal from amplifier 424.

Apparatus 14 also includes a beam splitter 414 that diverts 10% of combined beam 411 to a focusing lens 417 and a camera 418. Lens 417 and camera 418 together form a microscope imaging system that is used to observe beams 101 and 102 (FIG. 1B) on wafer 105, in order to focus combined beam 411 (FIG. 3) within region 103R (FIG. 1B) on wafer 105 (e.g., relative to other features on wafer 105).

The predetermined frequency f at which heating beam 101 is modulated can be made as low as necessary to provide a low noise bandwidth required in a particular case. However, as frequency f is reduced, lock-in amplifier 422 (FIG. 4) must observe an increasing number of cycles of the modulation, thereby increasing the measurement time and decreasing the throughput. A predetermined frequency of 100 Hz allows measurement in a period of 0.1 sec that is typically compatible with commercial throughput requirements for processing production wafers, e.g., 2 minutes per wafer may be provided for the inspection of 13 sites on wafer 105 (FIG. 1A). Under these conditions, the measurement period of 0.1 sec per site is negligible, and most of the throughput time may be used to load and position wafer 105 in measurement apparatus 14.

The above-described method 200 uses one or more of the following relationships (under steady-state conditions) between conductive region 103R's thermal conductivity, electrical resistance, and reflectance to provide a non-destructive yet reliable method for detecting changes in the resistance of layer 103. Specifically, the laser power absorbed in a layer 103 of thickness t is given by the difference between the incident power and the power at a depth t:

$$P_{abs} = P_{inc} - P(t) = P_{inc}(1 - e^{-\alpha t}) \quad (3)$$

where $P_{abs}$ is the absorbed power, $P_{inc}$ is the incident power, and $\alpha$ is the absorption coefficient. $\alpha$ is related to the extinction coefficient, which is the imaginary part of the index of refraction, according to the equation $$\alpha = 4\pi \frac{\kappa}{\lambda} \quad (4)$$

where $\lambda$ is the wavelength and $\kappa$ is the extinction coefficient. The paper entitled "Spectroscopic ellipsometry investigation of nickel silicide formation by rapid thermal process" by Yaozhi Hu and Sing Pin Tay, Journal of Vacuum Science Technology, volume 16, no. 3, published May/June 1998 by the American Vacuum Society (incorporated by reference herein in its entirety) gives values for the extinction coefficient of nickel silicide at various anneal temperatures. $\kappa$ may vary over a range of 2–3 at a wavelength of 700 nm and annealing temperatures in the range of 400–800° C. A larger range may be possible at 830 nm over an annealing temperature range of 200 to 1000° C. The temperature rise under beam 101 is estimated by solving the diffusion equation (1) in the half space under the incident beam 101 of radius $w_0$. This solution is $$T(w_0) - T_0 = \frac{2P_{inc}(1 - e^{-\alpha t})}{\pi k w_0} \quad (5)$$

where, k is the thermal conductivity of the silicon substrate and $T_0$ is the ambient temperature. Equation (5) shows that the temperature under the spot is a function of the thickness of the silicide film t and the absorption coefficient α, which varies with the silicide phase, as indicated in the paper by Hu and Tay. For a laser power of 10 mW and a beam diameter of 2 μm, equation (5) indicates heating in the range of 20 to 35° C. for a 300 angstrom thick film, for phases with extinction coefficients in the range of 1.5 to 4.

As noted above, line 301 (FIG. 3) shows an empirical correlation between the signal in microvolts and the sheet resistance of the same silicide samples reported in the paper of Hu and Tay. Note that line 301 provides a monotonic relationship between power of the reflected signal and the sheet resistance for test wafers. Line 301 can thus be used to relate the signal to the sheet resistance of a production wafer. For example, a signal of 270 microvolts from a production wafer corresponds to a sheet resistance of 10 ohms/square.

Note that region 103R (also called "feature") can be smaller than the diameter of combined beam 411. This is because the absorption length in layer 103 is several orders of magnitude shorter (e.g. for a layer 103 formed by cobalt silicide) than the absorption length in underlying layer 108 (at a wavelength of 830 nm). If the feature covers about 10% of the beam area, the absorption in the feature (i.e. region 103R) is still two orders of magnitude greater than the absorption in the underlying layer 108. Thus, a combined beam 411 of 2 micron diameter is used (in one embodiment) to make measurements on features smaller than 0.2 microns wide.

In one embodiment, layer 103 (also called "film") is partially absorbing, thereby to provide good resolution of the sheet resistance. In one example of this embodiment, layer 103 is thin enough so that a significant fraction of the laser light used for heating, say 90%, transmits through layer 103 to the underlying layer 108.

Furthermore, the method and apparatus can also be used with films that are substantially absorbing (less than 10% transmissive). By way of example, a data point 306 for a 600 angstrom titanium silicide film is shown in FIG. 3. This point 306 falls approximately on line 301 for the NiSi data. A TiSi film of this thickness is greater than 90% absorbing, and can be used with methods of the type described in U.S. patent application, Ser. No. 09/095,805 that is incorporated by reference herein in its entirety.

According to equation (3), the temperature under the spot is a function of the spot diameter. This assumes that diffusion of heat in the film is negligible compared to diffusion of heat in the silicon, which is true for thin films (e.g., films that are greater than 50% transmissive). For thicker films, however, heat diffuses radially in the film as well, increasing the effective spot diameter and reducing the temperature. The diffusion is a function of the film thickness and the crystalline phase—which determines the thermal conductivity of the film. So, a temperature rise in thicker films relates to both the crystalline phase and the inverse of the film thickness, and therefore also relates in a monotonic manner to the sheet resistance. Therefore, the same method (e.g., in either of FIGS. 2A and 2B) is used for thicker films.

An alternate embodiment uses an interferometer to measure changes in stress at an interface 112 (FIG. 1 B) between layers 103 and 108 that are induced by the difference in thermal expansion between layers 103 and 108. In this embodiment, beam 102 is a coherent laser beam. The phase and polarization of the reflection of beam 102 from layer 103 is measured by interfering the reflection with a reference beam that is coherent with beam 102. The change in stress at interface 112 induces a birefringence (difference in optical properties such as the index of refraction in different directions). This birefringence causes a rotation in the polarization of the reflected beam that is a function of the temperature of layer 103. Thus, the change in temperature may be measured, with the temperature a function of thickness of layer 103 and of the layer 103 crystalline phase of the material in layer 103.

Figure 5:
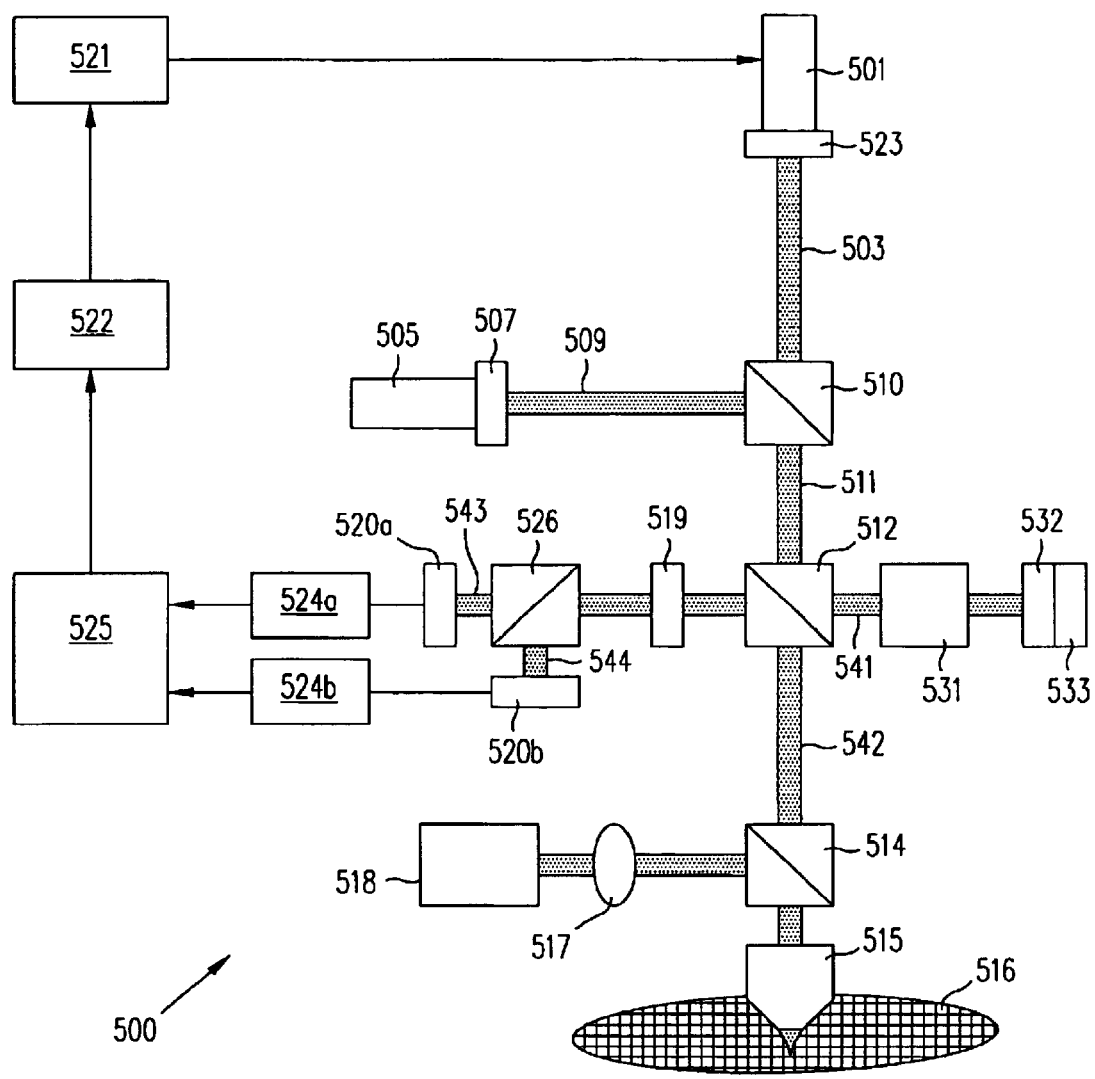

Apparatus 500 (FIG. 5) that is used in this embodiment is identical to apparatus 14 (FIG. 4) described above, except for the following differences. Note that many of the reference numerals in FIG. 5 are obtained from reference numerals of the corresponding parts in FIG. 4 by adding 100. In apparatus 500, laser 405 of apparatus 14 is replaced with laser 505 (e.g., model 6702-H1 a 0.98 μm 50 mW DBR laser available from Spectra Diode Labs, San Jose, Calif.). Laser 505 has a coherence length of several meters, making it more suitable for use in an interferometer because matching the length of the two arms of the interferometer is less critical. In apparatus 500, a reference beam arm 541 is added, and includes variable compensator 531 (e.g., model 5540, New Focus, Sunnyvale, Calif.), mirror 532, and piezoelectric positioner 533. Compensator 531 is set to ¼ wave, in order to rotate the polarization of reference beam 511 by 90° with respect to beam 542 reflected from wafer 516. Piezoelectric positioner 533 may be used to vary the phase of reference beam 541, in order to maximize the signal sensed by detectors 520a and 520b.

Polarizing beam splitter 526 is added in apparatus 500, and is oriented at 45° to the polarization of reference beam 541 and the reflection beam 542 from the wafer. The result is to crate sum and difference beams 543 and 544 that illuminate detectors 520a and 520b. The output from these detectors goes to transimpedance amplifiers 524a and 524b, which convert the output currents to voltages. The difference between the signals from the sum and difference amplifiers 524a and 524b is taken in difference amplifier 525. The difference signal is then sent to lock-in amplifier 522.

The operation of the interference mode is described in terms of the electric field in the reference beam and the beam returning from the sample. Compensator 531 is set to act like a quarter wave plate, which causes the polarization of reference beam 541 to be orthogonal to and 90° out of phase with respect to beam 511 propagating to wafer 516.

The reflection from layer 103 causes a phase shift δ and a polarization rotation. The rotation results in a component of the reflection beam 542 having the same polarization as reference beam 541. The electric field in the two polarization directions s and p can be written as follows:

$$E_s = E_r e^{j\pi/2} + E_{ws} e^{j\delta} \quad (6a)$$

$$E_p = E_{w0} + E_{wp} e^{j\delta} \quad (6b)$$

where $E_r$ is the electric field in the reference beam 541, $E_{ws}$ and $E_{wp}$ are the components of the reflection from wafer 516 that change with respect to temperature lying in the s- and p-polarization directions, and $E_{w0}$ is the electric field of the main reflection from wafer 516. Polarizing beam splitter 526 is oriented at 45° to the s- and p-polarization directions. This results in sum and difference components directed at detectors 520a and 520b; the electric fields of these components are $$E_{\pm} = \frac{1}{\sqrt{2}}[(E_r e^{j\pi/2} + E_{wp}e^{j\delta}) \pm (E_{w0} + E_{wp}e^{j\delta})] \quad (7)$$

The power in detectors 520a and 520b is the squared magnitude of the field. The signal at the lock-in is the difference between the signals at the two detectors, 520a and 520b proportional to the power at detectors 520a and 520b. Discarding terms of second order, the lock-in signal is $$P = P_+ - P_- \propto |E_+|^2 |E_-|^2 = 2[E_{w0}E_{wp} + \delta E_r E_{ws}] \quad (8)$$

The first term is due to polarization rotation, and would be seen if the reference beam 541 is blocked. The second term is due to induced phase shift. Note that the two terms could be measured individually by taking the difference in signals with and without the reference beam blocked. It is also possible to measure the intensity reflection from the exposed surface of layer 103 using the dc value of the reflection signal 542. This allows calculation of the index of refraction of the material at the exposed surface of layer 103, since the reflection coefficient of the laser power is $$R = \frac{(n-1)^2}{(n+1)^2} \quad (9)$$

Knowledge of the index of refraction allows determination of the crystalline phase, and, therefore, the resistivity, independent of the thickness, since the sheet resistance is related to the thickness and resistivity according to $$R_s = \frac{\rho}{t} \quad (10)$$

where $R_s$ is the sheet resistance, $\rho$ is the resistivity and $t$ is the thickness. In addition, it is possible to use a wavelength such that the photon energy for both lasers 501 and 505 lies at or below the bandgap of the semiconductor. For example, lasers with wavelength of 1.08 and 1.48 $\mu$m (corresponding to photon energies of 1.15 and 0.87 eV respectively) could be used, thereby to minimize carrier generation in layer 108. Reflection from carriers generated in layer 108 results in a signal from layer 108 that could potentially lead to errors in the measurement on a patterned structure (as opposed to a blanket deposited structure) where on or both beams' spot size is larger than, e.g. a line included in the pattern, because silicon surrounding the line is also illuminated and generates carriers which reflect the beam(s). Such an effect can be minimized by appropriate choice of wavelengths, e.g. below the bandgap of the semiconductor as described above (see, for example, the U.S. patent application, Ser. No. 09/095, 805, referenced above).

In addition, it is possible to use this method to measure properties of amorphized or damaged layers on the surface of a silicon wafer. One example of such a layer is an amorphization implant. In this process, a heavy dose of ions is implanted into the silicon surface to form an amorphous (non-crystalline) layer 103 within the first few hundred angstroms (typically <500 Å) of the surface 112. This implant is done with atoms that are not dopants, such as silicon or germanium. A second implant is then done into the amorphized layer 103 using dopant atoms such as boron or phosphorous. Normally, the boron or phosphorous implant would go relatively deep because the implanted atoms tend to follow channels in the crystal structure (a phenomenon known as channeling). The amorphizing implant breaks up the channels by disordering the crystal, allowing the boron or phosphorous implant to remain near the exposed surface of layer 103. A subsequent anneal at a temperature greater than 600° C. restores the crystal structure.

The disordered or amorphized layer has different thermal properties, and lower thermal conductivity than the underlying layer 108. It also has different optical absorption properties from crystalline silicon, with an absorption length about an order of magnitude shorter at a wavelength of 830 nm. Thus, the amorphized layer 103 acts very much like a deposited silicide layer. The surface temperature of that layer is a function of the thickness of layer 103, and the measurement described here can be used to measure the uniformity of properties of layer 103 such as thickness.

Numerous modifications and adaptations of the above-described embodiments will become apparent to a person skilled in the art of using lasers to measure semiconductor properties. For example, in an alternative embodiment, instead of using a laser to generate heating beam 101 to change peak temperature Tp, another heat source (such as an electron gun and electron focusing column that forms an electron beam) is used to modulate the temperature T of a conductive line in a wafer. Use of electrons in beam 101 instead of photons allows the diameter of beam 101 to be made smaller than possible when using photons. However, use of electrons in beam 101 requires measurement apparatus 13 to include a vacuum chamber to contain the electron source.

Note that the optically absorbing layer can be any of: (1) electrically conductive or (2) semiconductive (e.g., can be highly doped silicon) depending on the integrated circuits formed by use of such layers. In another embodiment, measurements are performed on an unpatterned layer of conductive material, such as a layer 103 prior to etching and formed by blanket deposition over all regions of a wafer.

Note that the above-described method and apparatus can be used with any silicide, such as titanium, cobalt, nickel or platinum. The method and apparatus can also be used with thin, partially transmissive films of other materials such as titanium, cobalt, nickel, platinum or aluminum, even if these films have not been annealed.

Also, in one embodiment, the probe beam illuminates a region that is larger than an individual feature (such as a trace) in the optically absorbing layer, so that the measurement does not resolve individual features in the illuminated region, and instead indicates an average measure of a property of such features, as described in in U.S. patent application, Ser. No. 09/521,232 that was incorporated by reference above.

A method of the type described herein can be practiced on a conductive layer 103 that is polysilicon, or polysilicon with a silicided top surface (polycide). Layer 103 can also be either polysilicon or polycide, and also an insulator layer may be located between layer 103 and an underlying substrate.

Therefore, numerous such modifications and adaptations of the above-described embodiments are encompassed by the attached claims.

What is claimed is:

1. A method for determining a property of a portion of a structure having a first layer and at least one underlying layer in contact with the first layer, the method comprising:

heating a region of the first layer using power modulated at a frequency that is predetermined to be sufficiently low to ensure that temperature of said region varies substantially linearly relative to said modulated power;

wherein the first layer comprises at least one crystalline phase from among a plurality of crystalline phases of a compound of a material comprised in said underlying layer, said crystalline phase depending on at least one process condition used in forming the first layer by annealing; and wherein the first layer partially absorbs and partially transmits the power;

measuring a signal indicative of a change in reflectivity of said first layer due to a corresponding temperature change in the first layer caused by said heating;

using said measured signal to determine an electrical conductive property of said first layer, said electrical conductive property depending on crystalline phase.

2. The method of claim 1 wherein:

the predetermined frequency is smaller than a maximum frequency beyond which nonlinearities in temperature response of said region become measurable.

3. The method of claim 2 wherein:

said maximum frequency is approximately 100 kHz.

4. The method of claim 2 further comprising:

changing a process parameter used in fabricating said structure in response to at least a predetermined change in said measured signal in multiple regions across said structure.

5. The method of claim 2 wherein the predetermined frequency is less than:

$$\frac{k}{2\pi\rho c\lambda^2}$$

wherein:

k is thermal conductivity of the region;

p is the density of the region;

c is the specific heat; and

λ is wavelength of a wave solution to a diffusion equation for heat transfer from the region.

6. The method of claim 2 further comprising:

comparing the power obtained from said measuring with a predetermined limit.

7. The method of claim 2 wherein:

the region of the first layer is heated by use of a first beam and said measuring comprises use of a second beam; and said measuring also comprises using a narrow band filter tuned to the wavelength of said second beam to filter out at least another portion of said first beam reflected by said region.

8. The method of claim 2 wherein:

the region of the first layer is heated by use of a first beam and said measuring comprises use of a second beam of a second power; and the second power is sufficiently low to ensure that less than 10% of heat generated in said region is due to the second beam.

9. The method of claim 1 wherein:

said measuring includes using a lock-in amplifier tuned to said predetermined frequency.

10. The method of claim 1 wherein said region is hereinafter referred to as "first region", the method further comprising:

focusing the first beam on a second region different from said first region; and repeating said measuring in said second region.

11. The method of claim 10 further comprising:

changing a process parameter used in fabricating said structure if the power measured in said region is nonuniform relative to the power measured in said second region.

12. The method of claim 1 wherein:

wherein the predetermined frequency is sufficiently low to ensure that an instantaneous temperature in said region is approximately equal to another temperature obtained in said region by heating with an unmodulated beam having a power equal to an instantaneous value of said first power.

13. The method of claim 1 wherein:

the first layer comprises a silicide as said compound.

14. The method of claim 13 wherein:

the underlying layer comprises polysilicon.

15. The method of claim 13 wherein:

the underlying layer comprises a silicon substrate.

16. The method of claim 1 wherein:

the first layer is one of polysilicon and polycide, and said at least one underlying layer is an insulator layer located between said first layer and an underlying substrate.

17. The method of claim 1 wherein:

the first layer has an optical absorption coefficient α that is several orders of magnitude greater than the corresponding absorption coefficient of said underlying layer.

18. The method of claim 1 wherein:

the first layer comprises silicon germanium.

19. The method of claim 1 wherein:

the first layer is less thermally conductive than the underlying layer.

20. The method of claim 1 wherein:

the underlying layer comprises a semiconductor.

21. The method of claim 20 wherein:

the compound is a metal compound.

22. The method of claim 21 wherein:

the metal compound is nickel silicide.

23. The method of claim 21 wherein:

the metal compound is cobalt silicide.

24. The method of claim 1 wherein:

the electrical conductive property is sheet resistance.

25. An apparatus for evaluating an annealed structure, said annealed structure comprising a partially transmissive electrically conductive layer, said layer comprising at least one suicide among a plurality of silicides, said apparatus having a first line to be coupled to an annealing apparatus and a second line to be coupled to a metal formation apparatus, said apparatus comprising:

a first source of a first beam of photons having a first power modulated at a frequency sufficiently low to ensure transfer of a majority of heat from a region of said layer illuminated by said first beam by diffusion;

a second source of a second beam of photons having a second power sufficiently low to ensure that an instantaneous temperature in said region is approximately equal to another temperature obtained in said region by heating with an unmodulated beam having power of an instantaneous value of said first power; and a photosensitive element located in a path of a portion of said second beam after reflection from said region, said portion being modulated at said frequency of modulation of said first beam; and a computer coupled to said photosensitive element and programmed to determine if power of said portion of said second beam reflected by said region is at least greater than a predetermined power and if so the computer driving a signal active on the first line to the annealing apparatus or on the second line to the metal formation apparatus or both.

26. A method for evaluating a wafer, the method comprising:

focusing a beam on a partially transmissive electrically conductive layer in said wafer, the partially transmissive electrically conductive layer comprising at least one silicide among a plurality of silicides, whose roughness is a function of crystal phase, and wherein said one silicide is formed by annealing;

measuring reflectance of said beam from said layer; and correlating said reflectance from said layer to a previously determined value said previously determined value having been obtained from a previous reflectance measurement on a reference wafer.

27. The method of claim 26 further comprising:

performing a plurality of measurements of reflectance along a line, to identify variation in a property of said layer along said line.

28. The method of claim 26 wherein:

the partially transmissive electrically conductive layer has an optical absorption coefficient $\alpha$ that is several orders of magnitude greater than the corresponding absorption coefficient of a material that is underlying the partially transmissive electrically conductive layer in the wafer.

29. The method of claim 26 wherein:

the wafer comprises an underlying layer of polysilicon underneath the partially transmissive electrically conductive layer.

30. The method of claim 26 wherein:

the wafer comprises an underlying layer of crystalline silicon underneath the partially transmissive electrically conductive layer.

31. The method of claim 26 wherein:

the partially transmissive electrically conductive layer comprises silicon germanium.

32. The method of claim 26 wherein:

the partially transmissive electrically conductive layer comprises a metal compound.

33. The method of claim 32 wherein:

the wafer comprises an underlying layer beneath the partially transmissive electrically conductive layer, and the underlying layer comprises a semiconductor material.

34. The method of claim 26 wherein:

the partially transmissive electrically conductive layer is less thermally conductive than an underlying layer comprised in said wafer.

* * * * *